United States Patent
Gruba et al.

(10) Patent No.: US 11,426,233 B2
(45) Date of Patent: Aug. 30, 2022

(54) ABLATION DELIVERY USING A CATHETER HAVING A SEMIPERMEABLE INFLATABLE BALLOON STRUCTURE

(71) Applicants: Cardiac Pacemakers, Inc., St. Paul, MN (US); Mayo Foundation for Medical Education and Research, Rochester, MN (US)

(72) Inventors: Sarah M. Gruba, Vadnais Heights, MN (US); James P. Rohl, Prescott, WI (US); Samuel J. Asirvatham, Rochester, MN (US); Suraj Kapa, Rochester, MN (US); Chance M. Witt, Rochester, MN (US); Deepak Padmanabhan, Rochester, MN (US); Christopher V. DeSimone, Rochester, MN (US)

(73) Assignees: Cardiac Pacemakers, Inc., St. Paul, MN (US); Mayo Foundation for Medical Education and Research, Rochester, MN (US)

(*) Notice: Subject to any disclaimer, the term of this patent is extended or adjusted under 35 U.S.C. 154(b) by 1122 days.

(21) Appl. No.: 16/000,770

(22) Filed: Jun. 5, 2018

(65) Prior Publication Data
US 2018/0344393 A1 Dec. 6, 2018

Related U.S. Application Data

(60) Provisional application No. 62/515,981, filed on Jun. 6, 2017.

(51) Int. Cl.
*A61B 18/14* (2006.01)
*A61M 25/10* (2013.01)
(Continued)

(52) U.S. Cl.
CPC ......... *A61B 18/1492* (2013.01); *A61M 25/10* (2013.01); *A61B 2018/0022* (2013.01);
(Continued)

(58) Field of Classification Search
CPC ........ A61B 18/1492; A61B 2018/0022; A61B 2018/00077; A61B 2018/00232;
(Continued)

(56) References Cited

U.S. PATENT DOCUMENTS

| 5,423,744 A | 6/1995 | Gencheff et al. |
| 5,846,239 A | 12/1998 | Swanson et al. |

(Continued)

FOREIGN PATENT DOCUMENTS

| WO | 2014189887 A2 | 11/2014 |
| WO | 2018081323 A1 | 5/2018 |

OTHER PUBLICATIONS

International Search Report and Written Opinion issued in PCT/US2017/058376, dated Feb. 1, 2018, 11 pages.
(Continued)

*Primary Examiner* — Joanne M Hoffman
*Assistant Examiner* — Bo Ouyang
(74) *Attorney, Agent, or Firm* — Fish & Richardson P.C.

(57) ABSTRACT

Embodiments of the present disclosure relate to treating diseased tissue with ablation therapy. In an embodiment, an apparatus comprises a catheter having an elongate body extending between a proximal end and a distal end. The apparatus further includes a balloon structure arranged proximal to the distal end of the catheter, wherein the balloon structure has a first portion with a first permeability and a second portion with a second permeability such that the first permeability is different than the second permeability. In addition, the apparatus includes a first electrode arranged on or within the balloon structure and configured
(Continued)

to: transmit current through the first portion, receive current transmitted through the first portion or both.

16 Claims, 16 Drawing Sheets

(51) Int. Cl.
  *A61B 18/00* (2006.01)
  *A61N 1/05* (2006.01)
(52) U.S. Cl.
  CPC .............. *A61B 2018/00077* (2013.01); *A61B 2018/00232* (2013.01); *A61B 2018/00238* (2013.01); *A61B 2018/00255* (2013.01); *A61B 2018/00261* (2013.01); *A61B 2018/00351* (2013.01); *A61B 2018/00375* (2013.01); *A61B 2018/00488* (2013.01); *A61B 2018/00529* (2013.01); *A61B 2018/00577* (2013.01); *A61B 2018/00613* (2013.01); *A61B 2018/00702* (2013.01); *A61B 2018/00791* (2013.01); *A61B 2018/00839* (2013.01); *A61B 2018/00875* (2013.01); *A61B 2018/1472* (2013.01); *A61M 2025/105* (2013.01); *A61N 1/056* (2013.01)
(58) Field of Classification Search
  CPC ........... A61B 2018/00238; A61B 2018/00255; A61B 2018/00261; A61M 25/10; A61M 2025/105
  See application file for complete search history.

(56) References Cited

U.S. PATENT DOCUMENTS

| | | | |
|---|---|---|---|
| 2002/0198521 A1 | 12/2002 | Maguire | |
| 2007/0032787 A1* | 2/2007 | Hassett | A61B 18/1492 606/41 |
| 2009/0247933 A1 | 10/2009 | Maor et al. | |
| 2010/0256629 A1 | 10/2010 | Wylie et al. | |
| 2012/0303011 A1* | 11/2012 | Schaeffer | A61B 18/24 606/16 |
| 2015/0018817 A1* | 1/2015 | Willard | B29C 48/10 606/41 |
| 2016/0310200 A1* | 10/2016 | Wang | A61B 18/04 |
| 2018/0110563 A1 | 4/2018 | Rohl et al. | |

OTHER PUBLICATIONS

International Search Report and Written Opinion issued in PCT/US2018/036153, dated Sep. 14, 2018, 11 pages.

* cited by examiner

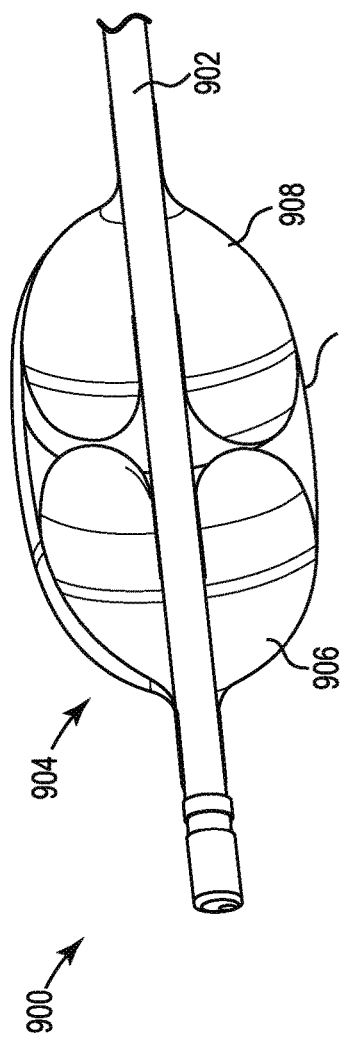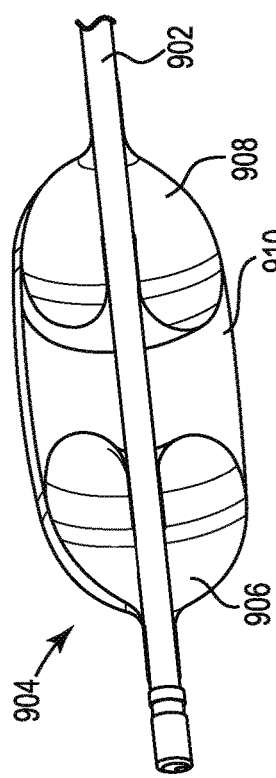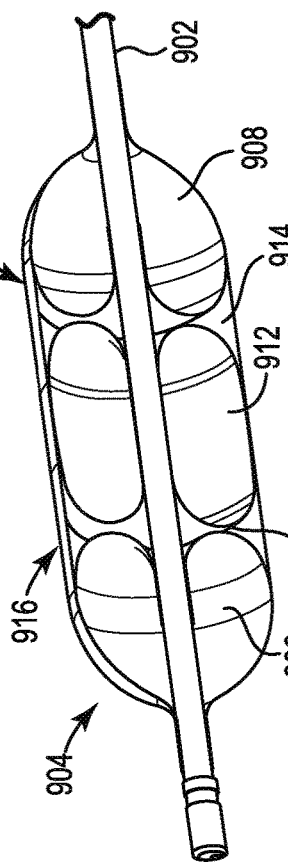

ABLATION DELIVERY USING A CATHETER HAVING A SEMIPERMEABLE INFLATABLE BALLOON STRUCTURE

CROSS-REFERENCE TO RELATED APPLICATION

This application claims priority to Provisional Application No. 62/515,981, filed Jun. 6, 2017, which is herein incorporated by reference in its entirety.

TECHNICAL FIELD

Embodiments of the present disclosure relate to providing therapy to a patient. More specifically, embodiments of the present disclosure relate to treating diseased tissue with ablation therapy.

BACKGROUND

Atrial fibrillation (AF) is an irregular and oftentimes rapid heart rate that commonly causes poor blood flow to the body of a patient experiencing AF. AF may be caused by diseased tissue in the heart that contributes to aberrant conductive pathways through the heart.

Ablation procedures, including ablation of thoracic veins such as the pulmonary vein, may be a treatment for AF. During pulmonary vein ablation, a catheter may be inserted into the atrium of a patient to target the diseased tissue causing the aberrant conductive pathway. After a portion of the catheter is positioned near the diseased tissue, the catheter may be configured to deliver energy to the diseased tissue. The delivered energy may permanently disrupt any conductive pathway through the diseased tissue, so that only normal conductive pathways are remaining in the heart, thereby alleviating the AF.

In certain instances, ablation may cause stenosis (e.g., narrowing of the vessels). Thus, there is a need in the art to provide solutions to this problem.

SUMMARY

Embodiments of the present disclosure include systems and methods for treating diseased tissue with ablation therapy. Example embodiments include, but are not limited to, the following.

In Example 1, an apparatus for applying ablation therapy to a tissue region comprises a catheter having an elongate body extending between a proximal end and a distal end; a balloon structure arranged near the distal end, the balloon structure comprising a first portion having a first permeability and a second portion having a second permeability, the first permeability differing from the second permeability; and a first electrode arranged on or within the balloon structure and configured to transmit or receive a current, wherein the current is transmitted or received through the second portion of the balloon structure via a liquid permeating the second portion, wherein the liquid cannot permeate the first portion.

In Example 2, the apparatus of Example 1, the liquid comprising at least one of saline, a pharmacological agent, a contrast agent, and an anti-stenotic agent.

In Example 3, the apparatus of any of Examples 1 and 2, the second permeability being due to the second portion having pores between approximately 1 millimeter and 10 millimeters when the balloon structure is in an expanded configuration.

In Example 4, the apparatus of any of Examples 1-3, the second portion having a strip shape extending circumferentially around the balloon structure.

In Example 5, the apparatus of any of Examples 1-4, the balloon structure having a third portion with a third permeability, the first portion being disposed between the second and third portions and the third permeability differing from the first permeability.

In Example 6, the apparatus of Example 5, the second permeability being substantially the same as the third permeability.

In Example 7, the apparatus of any of Examples 5 and 6, the first, second and third portions being arranged along an external surface of the balloon structure.

In Example 8, the apparatus of any of Examples 5-7, the second portion having a strip shape extending circumferentially around the balloon structure and the third portion having a strip shape extending circumferentially around the balloon structure, wherein the second and third portions have different axial positions along the balloon structure.

In Example 9, the apparatus of any of Example 5-7, the second and third portions being arranged along an external surface of the balloon structure and having a quadrilateral shape.

In Example 10, the apparatus of Example 9, the second and third portions having similar axial positions along the balloon structure and having different radial positions along the balloon structure.

In Example 11, the apparatus of Example 10, the second portion comprising a plurality of second portions and the third portion comprising a plurality of third portions, wherein each third portion of the plurality of third portions forms a pair with a respective second portion of the plurality of second portions.

In Example 12, the apparatus of any of Examples 1-11, further comprising a second electrode arranged on the distal end of the catheter, the second electrode configured to: receive the transmitted current of the first electrode or transmit the current received by the first electrode.

In Example 13, the apparatus of any of Examples 5-12, wherein a current is transmitted or received through the third portion of the balloon structure via a liquid permeating the third portion.

In Example 14, the apparatus of any of Examples 13, the balloon structure having a first chamber in fluid communication with the second portion and the balloon structure having a second chamber in fluid communication with the third portion, wherein the first and second chambers are in fluid isolation of one another.

In Example 15, the apparatus of Example 14, further comprising a second electrode arranged on or within the second chamber, wherein a current is at least one of: transmitted by the first electrode and received by the second electrode, and transmitted by the second electrode and received by the first electrode.

In Example 16, an apparatus for applying ablation therapy to a tissue region comprises: a catheter having an elongate body extending between a proximal end and a distal end; a balloon structure arranged near the distal end, the balloon structure comprising a first portion having a first permeability and a second portion having a second permeability, the first permeability differing from the second permeability; and a first electrode arranged on or within the balloon structure and configured to transmit or receive a current, wherein the current is transmitted or received through the second portion of the balloon structure via a liquid permeating the second portion, wherein the liquid cannot permeate the first portion.

In Example 17, the apparatus of Example 16, the liquid comprising at least one of saline, a pharmacological agent, a contrast agent, and an anti-stenotic agent.

In Example 18, the apparatus of Example 16, the second permeability being due to the second portion having pores between approximately 1 millimeter and 10 millimeters when the balloon structure is in an expanded configuration.

In Example 19, the apparatus of Example 16, the second portion having a strip shape extending circumferentially around the balloon structure.

In Example 20, the apparatus of Example 16, the balloon structure having a third portion with a third permeability, the first portion being disposed between the second and third portions and the third permeability differing from the first permeability.

In Example 21, the apparatus of Example 20, the second permeability being substantially the same as the third permeability.

In Example 22, the apparatus of Example 20, the first, second and third portions being arranged along an external surface of the balloon structure.

In Example 23, the apparatus of Example 20, the second portion having a strip shape extending circumferentially around the balloon structure and the third portion having a strip shape extending circumferentially around the balloon structure, wherein the second and third portions have different axial positions along the balloon structure.

In Example 24, the apparatus of Example 20, the second and third portions being arranged along an external surface of the balloon structure and having a quadrilateral shape.

In Example 25, the apparatus of Example 24, the second and third portions having similar axial positions along the balloon structure and having different radial positions along the balloon structure.

In Example 26, the apparatus of Example 25, the second portion comprising a plurality of second portions and the third portion comprising a plurality of third portions, wherein each third portion of the plurality of third portions forms a pair with a respective second portion of the plurality of second portions.

In Example 27, the apparatus of Example 16, further comprising a second electrode arranged on the distal end of the catheter, the second electrode configured to: receive the transmitted current of the first electrode or transmit the current received by the first electrode.

In Example 28, the apparatus of Examples 20, wherein a current is transmitted or received through the third portion of the balloon structure via a liquid permeating the third portion.

In Example 29, the apparatus of any of Examples 28, the balloon structure having a first chamber in fluid communication with the second portion and the balloon structure having a second chamber in fluid communication with the third portion, wherein the first and second chambers are in fluid isolation of one another.

In Example 30, the apparatus of Example 29, further comprising a second electrode arranged on or within the second chamber, wherein a current is at least one of: transmitted by the first electrode and received by the second electrode, and transmitted by the second electrode and received by the first electrode.

In Example 31, an apparatus for applying ablation therapy to a tissue region comprises: a catheter having an elongate body extending between a proximal end and a distal end; a balloon structure arranged near the distal end, the balloon structure comprising: a first portion having a first permeability; a second portion having a second permeability, a third portion having a third permeability, a first chamber in fluid communication with the second portion, and a second chamber in fluid communication with the third portion; a first electrode in fluid communication with the first chamber; and a second electrode in fluid communication with the second chamber, wherein the first and second electrodes are configured to conduct a current therebetween via a liquid that permeates the second and third portions, wherein the liquid cannot permeate the first portion.

In Example 32, the apparatus of Example 31, the liquid comprising at least one of saline, a pharmacological agent, a contrast agent, and an anti-stenotic agent.

In Example 33, the apparatus of Example 31, the second permeability being due to the second portion having pores between approximately 1 millimeter and 10 millimeters when the balloon structure is in an expanded configuration and the third permeability being due to the third portion having pores between approximately 1 millimeter and 10 millimeters when the balloon structure is in an expanded configuration.

In Example 34, the apparatus of Example 31, the second portion having a strip shape extending circumferentially around the balloon structure and the third portion having a strip shape extending circumferentially around the balloon structure, wherein the second and third portions have different axial positions along the balloon structure.

In Example 35, the apparatus of Example 31, the second and third portions having: similar axial positions along the balloon structure, different radial positions along the balloon structure, and quadrilateral shapes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 9A shows a partial cross-sectional illustration of another exemplary apparatus for applying stenosis prevention to a tissue region having a first multiple chamber configuration in accordance with embodiments of the disclosure.

FIG. 9B shows the apparatus for applying stenosis prevention, as shown in FIG. 9A, having a second multiple chamber configuration in accordance with embodiments of the disclosure.

FIG. 9C shows the apparatus for applying stenosis prevention, as shown in FIGS. 9A-B, having a third multiple chamber configuration in accordance with embodiments of the disclosure.

Figure 1:
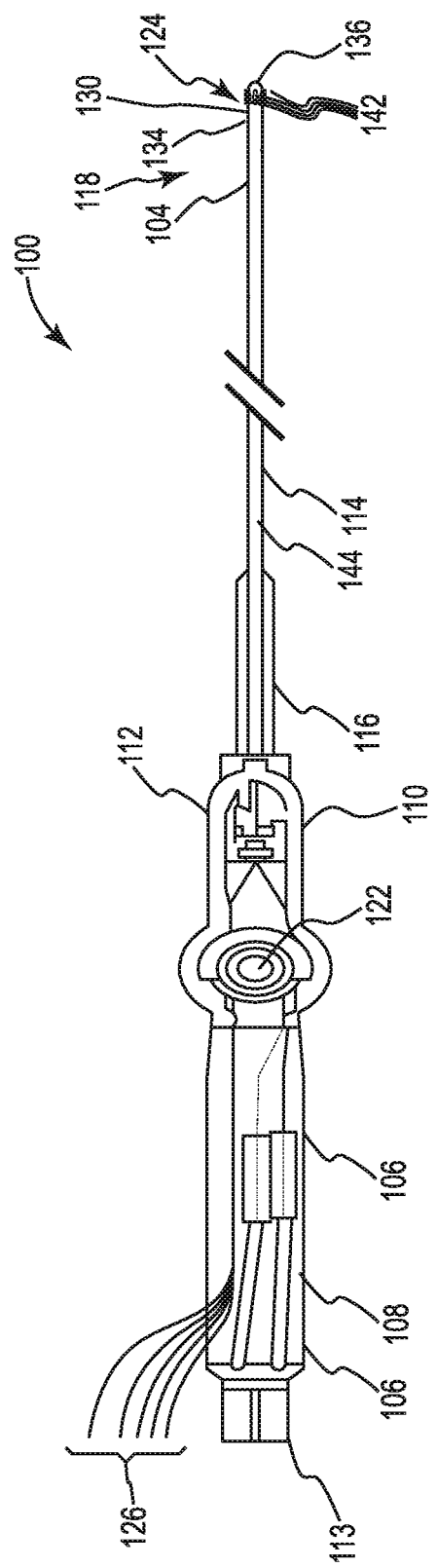
FIG. 1 shows an exemplary ablation system in accordance with embodiments of the disclosure.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

DETAILED DESCRIPTION

Embodiments of the present disclosure include systems and methods for treating diseased tissue with ablation therapy. According to embodiments, the systems and methods may be used to treat atrial fibrillation (AF). Additionally or alternatively, in embodiments, the systems and methods may be used as therapy to treat cancerous cells in, for example, the esophagus and/or liver of a patient.

FIG. 1 is a schematic diagram illustrating an ablation system 100, in accordance with embodiments of the disclosure. The system 100 includes a catheter 102 sized and shaped for vascular access. The catheter 102 has a distal end 104 and a proximal end 106. In embodiments, the proximal end 106 of the catheter 102 includes a handle 108 having a proximal portion 110 and a distal portion 112. A physician may manipulate the ablation system 100 via the handle 108 during a treatment procedure involving ablation. The handle 108 may include a plurality of conduits, conductors, and wires to facilitate control of the catheter 102 and/or mating of the catheter 102 with a source of fluid, a source of ablative energy, a source of mapping, temperature display, sensors, and/or control software/hardware. The handle 108 may further include a connection port 113 through which ablative energy source and a mapping energy source may be operably coupled.

According to embodiments, the catheter 102 may include an elongate body 114 having a proximal end 116 and a distal end 118. The elongate body 114 may house electrical conductors/cable assembly (e.g., wires) for transmitting sensed signals and/or ablation energy. In addition, the elongate body 114 may include a circular cross-sectional geometry. However, other cross-sectional shapes, such as elliptical, rectangular, triangular, and various other shapes, can be provided. In embodiments, the elongate body 114 may be preformed of an inert, resilient material that retains its shape and does not soften significantly at body temperature; for example, Pebax®, polyethylene, or Hytrel®) (polyester). The elongate body 114 may be made of a variety of materials, including, but not limited to, metals and polymers. The elongate body 114 may be flexible and capable of winding through a tortuous path that leads to a target site, e.g., an area within the heart, an area within a liver and/or an area within an esophagus. The elongate body 114 may also be semi-rigid, i.e., by being made of a stiff material, or by being reinforced with a coating or coil, to limit the amount of flexing.

In embodiments, the movement of the distal end 118 of the elongate body 114 (such as to wind through the tortuous path that leads to a target site) can be controlled by a control mechanism 122 included within the handle 108. The system 100 may include an articulating section of the elongate body 114 (e.g., near the distal end 118) that is controlled via the control mechanism 122. The distal end 118 of the elongate body 114 may be deflected or bent. The articulation section of the body may facilitate insertion of the catheter 102 through a body lumen (e.g., vasculature) and/or placement of electrodes at a target tissue location. The articulation may provide one or more degrees of freedom and permit up/down and/or left/right articulation.

The distal end 104 of the catheter 102 includes a tip section 124 positioned at the distal end 118 of the elongate body 114. The tip section 124 includes a proximal portion 134 and a distal portion 136. In embodiments, portions of the tip section 124 may be formed from a conductive material. For example, the system 100 may include one or more electrode structures 142, formed of the conductive material, on an exterior surface 130 of the tip section 124. The electrode structures 142 may be arranged around a circumference of exterior surface 130 of the tip section 124. In addition, the electrode structures 142 may be configured as mapping electrodes and/or ablation electrodes.

According to embodiments, the electrode structures 142 may be configured to conduct radio frequency (RF) energy or direct current to form lesions during the ablation procedure. For example, the electrode structures 142 may deliver ablation energy to the myocardial tissues that are the source of arrhythmia, thereby destroying them or a portion thereof through heat. Each of the electrode structures 142 may be coupled to one or more of the wires 126 using suitable means, such as soldering or welding. The number of wires 126 may be equal to the number of electrode structures 142. The wires 126 can pass through a lumen 144 extending through the elongate body 114 of the catheter 102 and are electrically coupled to the RF generator exteriorly coupled to the ablation system 100.

In embodiments, the electrode structures 142 may also be configured to measure the localized intracardial electrical activity (map) in real time at the point of RF energy delivery. The electrode structures 142 may allow a physician to ascertain lesion formation by measuring the electrical activity of the tissue having been in contact with an ablation electrode (e.g., the lack of near-field electrical activity may indicate ablated tissue, whereas the presence of near-field electrical activity may indicate near-field electrical activity may indicate live or non-ablated tissue). In embodiments, the wires 126, coupled to the electrode structures 142, may also be electrically coupled to a mapping signal processor such that electrical events in myocardial tissue can be sensed for the generation of electrograms, monophasic action potentials (MAPs), isochronal electrical activity maps, and the like. Additionally or alternatively, the electrode structures 142 may be used to measure impedance of tissue contacting the electrode structures 142. In embodiments, the impedance may be used to determine whether ablation has created irreversible electroporation for the tissue. For example, the measured impedance for tissue while being ablated may drop until the tissue is irreversibly electroporated at which time the impedance is constant.

Figure 2:
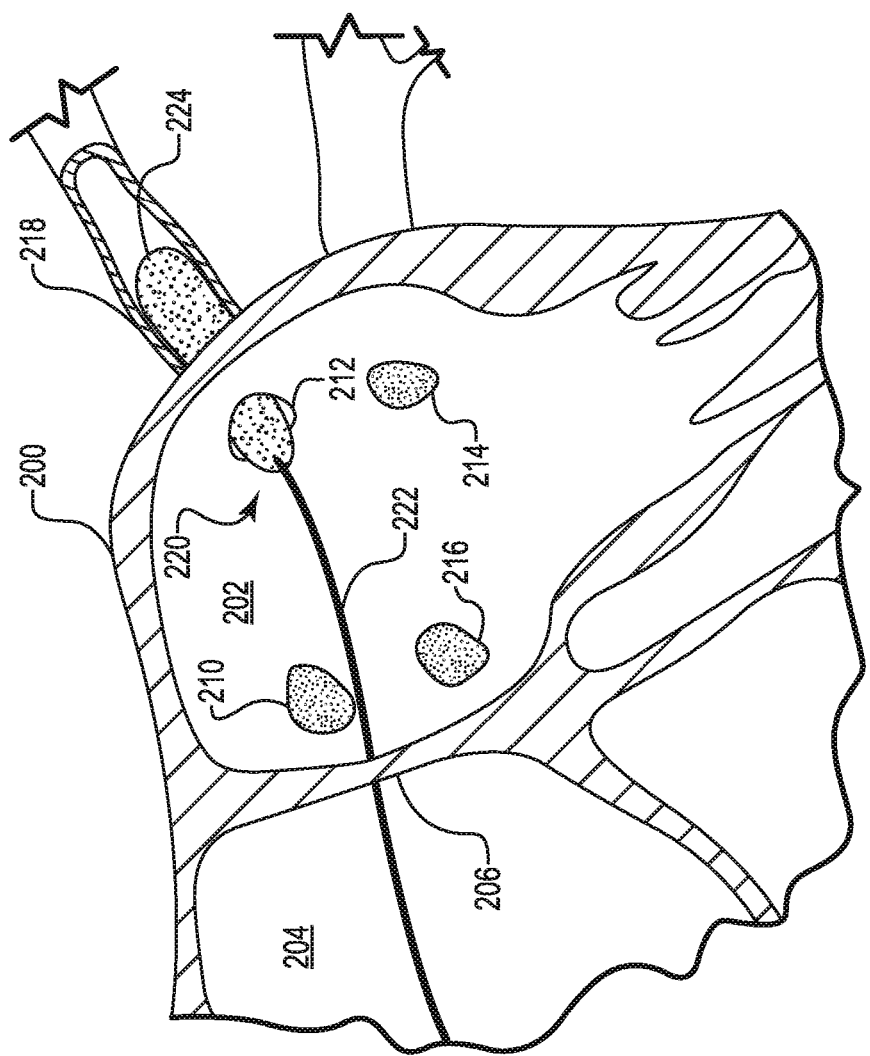
FIG. 2 shows an exemplary ablation system at a target tissue region within patient's heart in accordance with embodiments of the disclosure.

FIG. 2 is a diagram illustrating an ablation system located at a target tissue region within a patient's heart 200, in accordance with embodiments of the disclosure. The heart 200 depicted in FIG. 2 may be undergoing a pulmonary vein ablation procedure using a device 220 in accordance with various aspects discussed herein. In embodiments, the device 220 may be the same or similar to the system 100 discussed in relation to FIG. 1 above.

According to embodiments, the device 220 may include a catheter having an elongate body 222 that is connected to a balloon structure 224. The device 220 may be connected to an ablation energy source and controller (e.g., radiofrequency (RF) or direct current (DC) system not shown) and one or more liquid sources (not shown), both of which are located external to the patient. The balloon structure 224 may be located near the distal end of elongate body 222. One or more interior chambers of the balloon structure 224 may be in fluid communication with a liquid delivery lumen arranged within the elongate body 222. The liquid delivery lumen is used to convey the one or more liquids from the source external to the patient into the balloon structure 224. The elongate body 222 and the balloon structure 224 may be delivered to a tissue region to which ablation energy may be applied.

As shown in FIG. 2, the elongate body 222 may be positioned in the left atrium 202 of the patient's heart 200. For example, the device 220 may enter the right atrium 204 of heart 200 through a femoral vein and the inferior vena cava (not shown). After which, the device 220 may be passed through a puncture in an atrial septum 206 to access left atrium 202. From the left atrium 202, the balloon catheter device 220 may be positioned through any of the pulmonary vein ostia 210, 212, 214, or 216 to enter a pulmonary vein such as pulmonary vein 218. In embodiments, the device 220 may be an over-the-wire device that is delivered over or on a pre-placed guidewire and a delivery catheter/sheath or rapid exchange catheter may be used to assist in the insertion and placement of the device 220. Additionally or alternatively, the device 220 may include its own steering mechanism (not shown).

After positioning of the device 220 at the tissue region (within the pulmonary vein 218 as shown in FIG. 2), the balloon structure 224 may be expanded as shown in FIG. 2. The balloon structure 224 may be inflated using a liquid (e.g., saline, a pharmacological agent, a contrast agent, or a combination thereof) as the inflation medium. As an example, a 50/50 saline contrast mix may be used as the liquid to inflate the balloon structure 224. In instances where the balloon structure 224 is positioned within a vessel, such as the pulmonary vein 218, the inflation of balloon structure 224 may cause the outer surface of balloon structure 224 to contact an inner wall of vessel such as the pulmonary vein 218. In certain instances, ablation energy may be applied through one or more electrodes (not shown) arranged within the balloon structure 224 to initiate the modulation of target neural fibers. In embodiments, one or more portions of the balloon structure 224 may have a permeability such that a liquid may exude, elute, weep, or otherwise be transmitted through the one or more portions of the balloon structure 224. In embodiments, the liquid may be an anti-stenotic pharmaceutical agent that may contact the inner wall of pulmonary vein 218.

The ablation energy may be applied through one or more portions of the balloon structure 224 by an electric field generated by the external source/controller and transferred through wires within one or more lumens of the elongate body 222 to electrodes (not shown) arranged with the balloon structure 224. In embodiments, the electrical energy may be transmitted to the inner wall of pulmonary vein 218 directly from the electrodes on the surface of balloon structure 224 or indirectly from the electrodes within the balloon structure 224 via the liquid (pharmacological agent) that exudes from the exterior surface of balloon structure 224. The electric field may modulate the activity along neural fibers within the wall of the pulmonary vein 218 by at least partially causing apoptotic cell death to the tissue receiving the ablation energy. While the electric field for ablation is being applied, transmission of the liquid (pharmacological agent) from the balloon structure 224 to the tissue can be continued in embodiments. The ablation process may be performed simultaneously and concurrently with the delivery of an antimitotic pharmacological agent to the tissue receiving the ablation energy or the ablation process can be performed sequentially with the delivery of the liquid.

Delivering the pharmacological agent prior to the ablative energy may provide iontophoresis-like action to drive the agent into the tissue. Delivering the ablative energy prior to the pharmacological agent can provide some electroporative disruption of the endothelial cell-to-cell junction, and thereby promote delivery of the agent. In certain instances, a repetitious cyclic delivery of ablative energy and the pharmacological agent may enhance uptake of the agent. In certain instances, the pharmacological agent can have an ionic base so as to optimize the ablative energy's ability to get the agent beyond the endothelium of the tissue. Paclitaxel is an example of one type of antimitotic pharmacological agent that may be used with the apparatuses, systems, and methods discussed herein. This technique of coordinating the delivery of paclitaxel with the ablation process may prevent or reduce the occurrence of fibrosis, stenosis, and neointimal hyperplasia of the tissue undergoing ablation.

In embodiments, the electric field may be generated by applying direct current to the one or more electrodes arranged within the balloon structure 224. Application of direct current, which is a thermal, may be less likely to cause stenosis as compared to RF ablation. In certain instances, the amount of anti-stenotic pharmaceutical agent released from the balloon structure 224 may be tailored based on the type of energy used for ablation (e.g., a greater amount of anti-stenotic for RF ablation as compared to the amount of anti-stenotic for direct current). In addition, the use of direct current may cause apoptotic cell death to the tissue receiving the ablation energy. The direct current may form pores in the cells of the wall of the pulmonary vein 218 that are irreversible (e.g., the pores do not close). The balloon structure 224 being in contact with the wall of the pulmonary vein 218 may provide controlled and direct ablation of a target area while mitigating against down-stream proliferation of the ablation energy.

Figure 3:
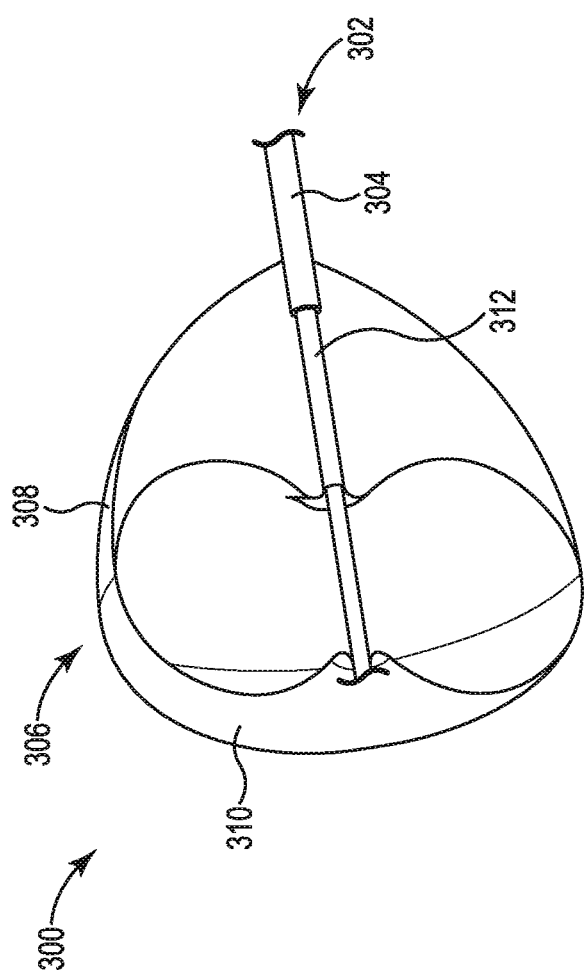
FIG. 3 shows a partial cross-sectional illustration of an exemplary apparatus for applying ablation therapy to a tissue region in accordance with embodiments of the disclosure.

FIG. 3 is a diagram illustrating a partial cross-section of an apparatus 300 for applying ablation therapy to a tissue region, in accordance with embodiments of the disclosure. The apparatus 300 may include a catheter 302 sized and shaped for vascular access that has an elongate body 304 extending between a proximal end and a distal end of the catheter 302. A distal portion of the catheter 302 and the elongate body 304 is shown in FIG. 3. The apparatus 300 may also include a balloon structure 306 arranged near the distal end of the elongate body 304. The balloon structure 306 may include a first portion 308 and a second portion 310. The balloon structure 306 may be configured to inflate in response to a liquid or inflation medium being provided thereto. In certain instances, the first portion 308 and the second portion 310 may be separately inflated using two inflation mediums or the first portion 308 and the second portion 310 may be inflated using a single inflation medium.

According to embodiments, the first portion 308 of the balloon structure 306 may include a first permeability and the second portion 310 of the balloon structure 306 may include a second permeability. The first permeability may differ from the second permeability. More specifically, the first permeability may be greater than the second permeability. As a result and in certain instances, the first portion 308 of the balloon structure 306 may be configured to permeate a liquid therethrough. As the first portion 308 of the balloon structure 306 is inflated, the liquid may permeate therethrough. The liquid may be, for example, saline, a pharmacological agent, a contrast agent, an anti-stenotic agent, or a combination thereof. As an example, a 50/50 saline contrast mix may be used as the liquid.

In embodiments, the first portion 308 of the balloon structure 306 may form a first chamber, and the second portion 310 of the balloon structure 306 may form a second chamber. As a result, the first portion 308 and the second portion 310 may be separate and distinct structures. For example, the second portion 310 may be a balloon or other similar structure that is arranged within the first portion 308. The first portion 308 may be deposited or attached onto the second portion 310.

In embodiments, the apparatus 300 may also include one or more electrodes 312 arranged on or within the balloon structure 306. As shown, the electrode 312 is arranged within the balloon structure 306. The electrode 312 may be configured to deliver energy to a tissue region. In certain instances, the electrode 312 may be configured to delivery energy in response to a direct current applied thereto.

Figure 4:
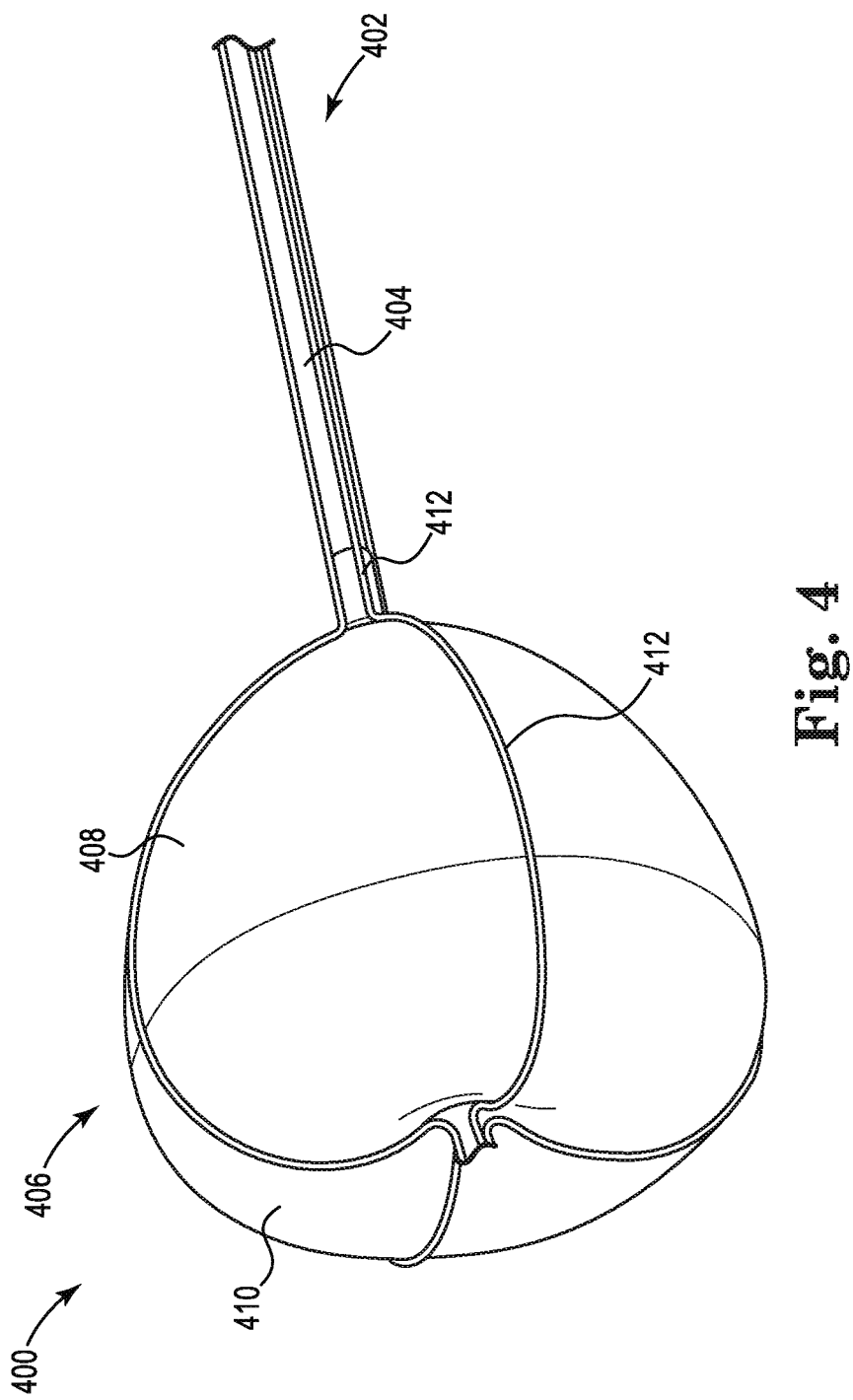
FIG. 4 shows an exemplary apparatus for applying ablation therapy to a tissue region in accordance with embodiments of the disclosure.

FIG. 4 is a diagram illustrating an apparatus 400 for applying ablation therapy to a tissue region, in accordance with embodiments of the disclosure. The apparatus 400 may include a catheter 402 having an elongate body 404. A distal portion of the catheter 402 and the elongate body 404 is shown in FIG. 4. The apparatus 400 may also include a balloon structure 406 arranged near the distal end of the elongate body 404. The balloon structure 406 may include a first portion 408 having a first permeability and a second portion 410 having a second permeability. The balloon structure 406 may be configured to inflate in response to a liquid or inflation medium being provided thereto. The first permeability may differ from the second permeability such that the first permeability may be greater than the second permeability. In embodiments, the first portion 408 of the balloon structure 406 may be configured to permeate a liquid therethrough, and the second portion 410 may mitigate against liquid permeation or eluting. Thus, as the balloon structure 406 is inflated, the liquid may permeate through the first portion 408. The liquid may be, for example, saline, a pharmacological agent, a contrast agent, an anti-stenotic agent, or a combination thereof. As an example, a 50/50 saline contrast mix may be used as the liquid.

In embodiments, the apparatus 400 may include electrodes 412 arranged on an exterior surface of the balloon structure 406. The electrodes 412 may be arranged along the elongate body 404 and configured to deliver energy to a tissue region. The electrodes 404 may also be arranged uniformly or non-uniformly about the circumference of the balloon structure 406. In embodiments, the electrodes 412 may be configured to delivery energy in response to a direct current applied thereto. Energy may be delivered simultaneously/concurrently on the electrodes 412 or sequentially across the electrodes 412 via radiofrequency energy, electroporation, vibration, ultrasound or laser energy.

Figure 5:
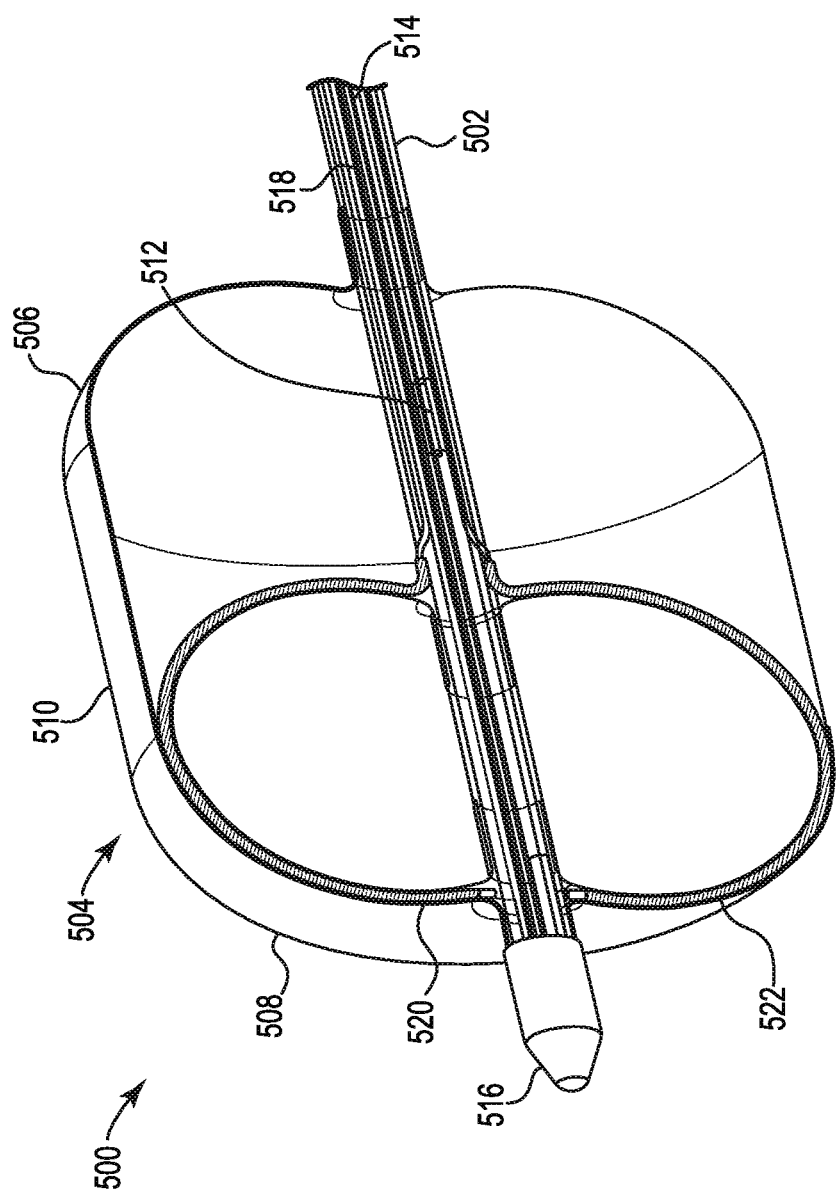
FIG. 5 shows a partial cross-sectional illustration of another exemplary apparatus for applying ablation therapy to a tissue region in accordance with embodiments of the disclosure.

FIG. 5 is a diagram illustrating a partial cross-section of another apparatus 500 for applying ablation therapy to a tissue region, in accordance with embodiments of the disclosure. The apparatus 500 includes a catheter having an elongate body 502. At or near a distal portion of the elongate body 502 is a balloon structure 504. The balloon structure 504 may be attached to or formed on the elongate body 502.

The balloon structure 504 may include a first portion 506, at least a section of which includes a first permeability, and a second portion 508 having a second permeability. The balloon structure 504 may be configured to inflate in response to a liquid or inflation medium being provided thereto. In embodiments, the first permeability may be greater than the second permeability. Thus, in embodiments, the first portion 506 of the balloon structure 504 may be configured to permeate a liquid therethrough (in response to inflation of the balloon structure 504) and the second portion 508 of the balloon structure 504 may be to anchor the elongate body 502 at a tissue region. The first portion 506 and the second portion 508 are arranged along an external surface of the balloon structure 504.

According to embodiments, the first portion 506 of the balloon structure 504 may form a first chamber, and the second portion 508 of the balloon structure 504 may form a second chamber. The second portion 508 may be a balloon or other similar structure that is arranged within the first portion 506. The first portion 506 may be deposited or attached onto the second portion 508. As noted above, at least a section of the first portion 506 has a greater permeability than the second portion 508. In embodiments, the permeability of the second portion 508 may be zero such that liquid does not permeate or elute therethrough. Thus, for example, at least a section 510 of the balloon structure 504 that does not include the second portion 508 may be permeable. The first portion 506 may be formed of the same permeability such that the entirety of the first portion 506 may permeate liquid therethrough, or the section 510 of the first portion 506 may permeate liquid therethrough.

The balloon structure 504 may be positioned at a target tissue region for ablation. In certain instances, the tissue region may be a vessel such as a pulmonary vein or a renal vein or other appendage. The balloon structure 504 may be configured to deploy within the vessel such that the section 510 contacts the vessel wall. The first portion 506 may permeate the liquid to the tissue region (e.g., the vessel wall). The liquid may include an anti-stenotic agent that mitigates against stenosis at the tissue region. In addition, the second portion 508 may be configured to anchor the elongate body 502 at the tissue region. The second portion 508 may be impermeable to the liquid.

The apparatus 500 may also include an electrode 512 arranged within the balloon structure 504. The electrode 512 may be configured to deliver energy to a tissue region. In certain instances, the electrode 512 may be arranged within the first portion 506 and configured to delivery energy in response to a direct current applied thereto. The ablation energy from the electrode 512 may be applied through an external surface of the first portion 506 of the balloon structure 504 by an electric field generated by the external source/controller and transferred through a wire 514 within the elongate body 502. The electric energy can be transmitted to the tissue region (e.g., the vessel wall) via the liquid, which may include an anti-stenotic agent, that exudes from the first portion 506 of the balloon structure 504. The electric field may modulate the activity along neural fibers within the wall of the tissue by at least partially causing apoptotic cell death to the tissue receiving the ablation energy. In certain instances while the electric field for ablation is being applied, transmission of the liquid, including the anti-stenotic agent, from the first portion 506 of the balloon structure 504 to the tissue can be continued. The ablation process applied via the electrode 512 may be performed simultaneously and concurrently with the delivery of an antimitotic pharmacological agent to the tissue receiving the ablation energy or the ablation process can be performed sequentially with the delivery of the liquid.

In certain instances and as noted above, the electric field may be generated by applying direct current to the electrode 512. The use of direct current may cause apoptotic cell death to the tissue receiving the ablation energy. The direct current may form pores in the cells of the tissue region such that are irreversible (e.g., the pores do not close). The balloon structure 504 being in contact with the tissue may provide controlled and direct ablation of a target area while mitigating against down-stream proliferation of the ablation energy.

The apparatus 500 may also include a tip electrode 516 that is configured to form a ground or a closed-loop with the electrode 512. Similar to the electrode 512, the tip electrode 516 may be coupled to the external source/controller via a wire 518 within the elongate body 502. The external source/controller may apply RF ablation energy or DC current. Thus, the tip electrode 516 may function as a single point ablation electrode when the external source/controller is configured to apply RF ablation energy.

Figure 7:
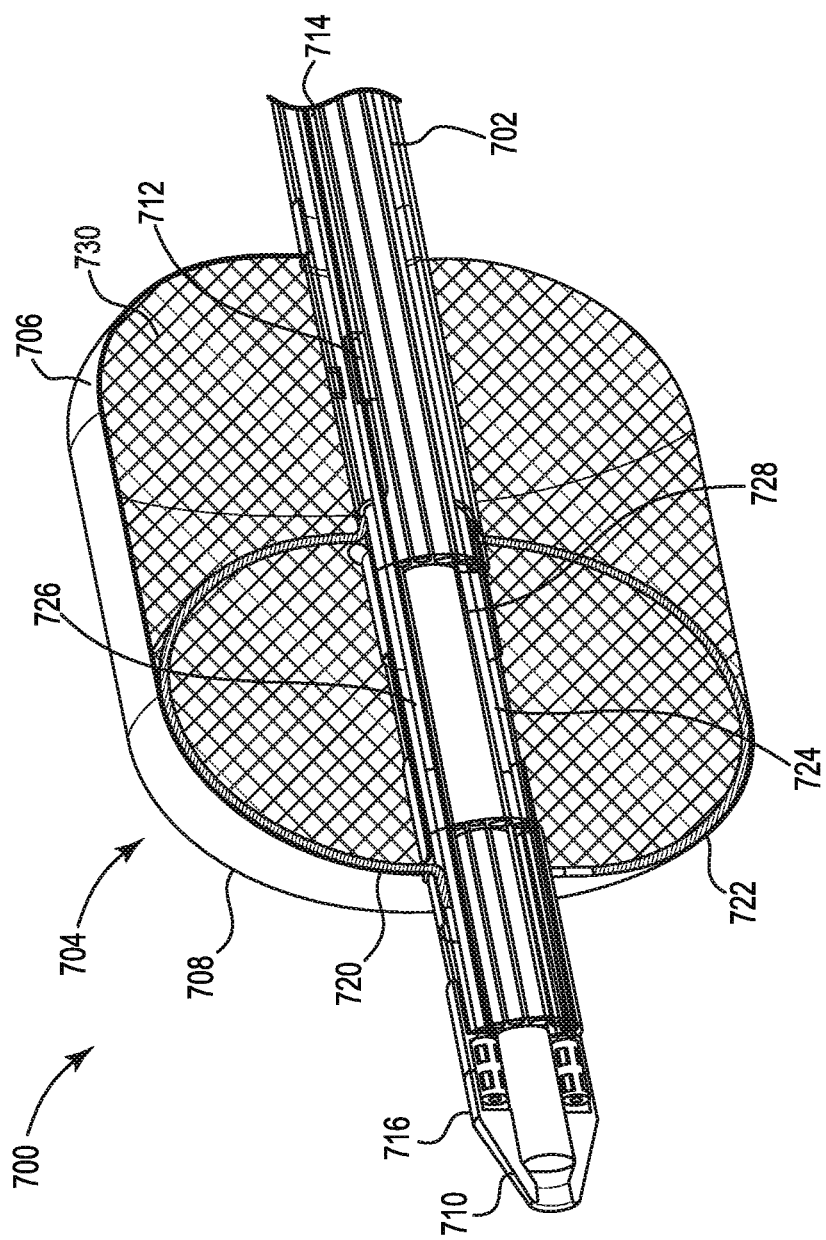
FIG. 7 shows a partial cross-sectional illustration of another exemplary apparatus for applying ablation therapy to a tissue region having a steering mechanism in accordance with embodiments of the disclosure.
Figure 8:
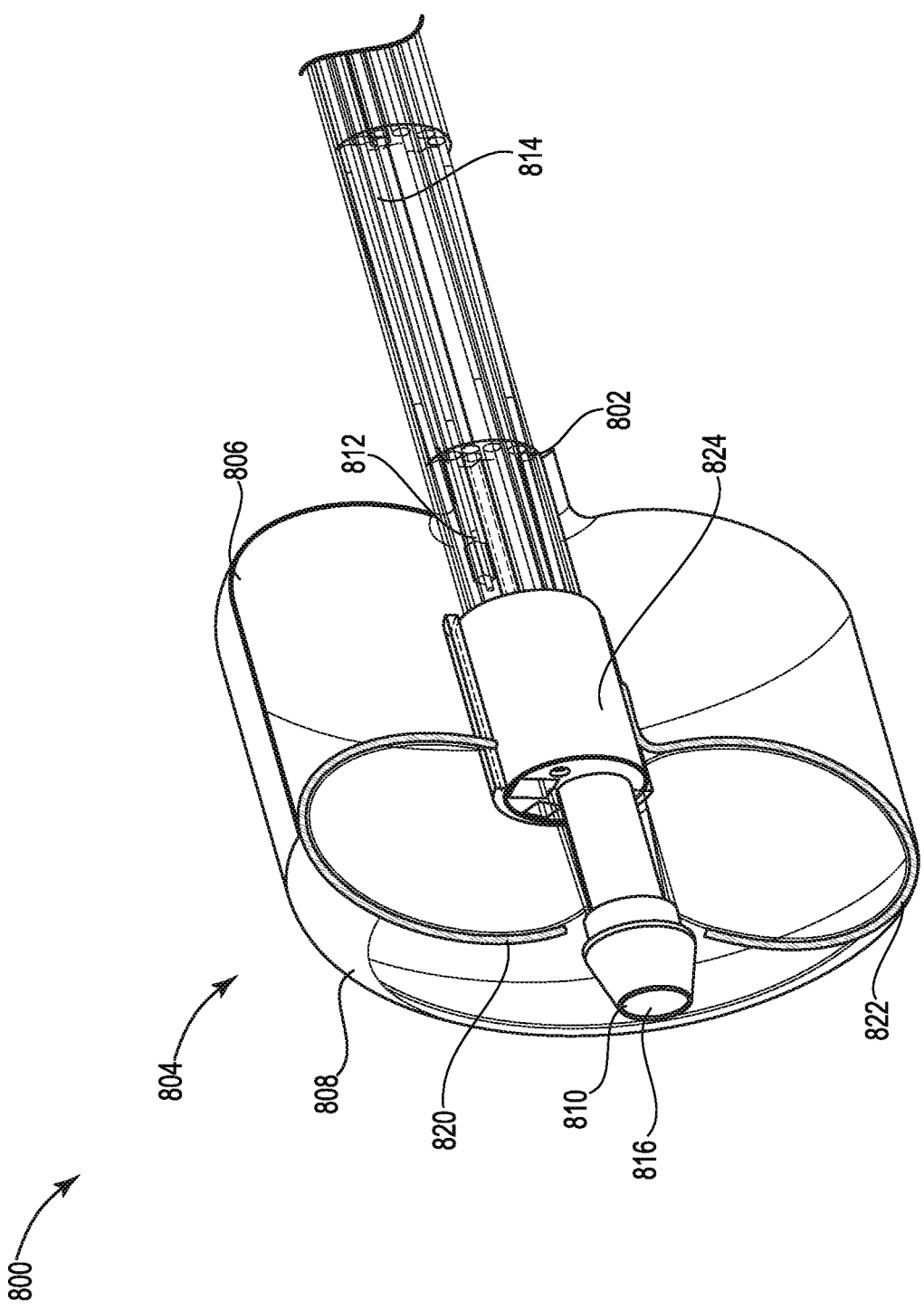
FIG. 8 shows a partial cross-sectional illustration of another exemplary apparatus for applying ablation therapy to a tissue region having a visualization element in accordance with embodiments of the disclosure.

In embodiments, the electrode 512 and/or the tip electrode 516 may also be configured to measure the localized intracardial electrical activity. The wire 514 and/or the wire 518 may also be electrically coupled to a mapping signal processor such that electrical events in myocardial tissue can be sensed for the generation of electrograms, monophasic action potentials (MAPs), isochronal electrical activity maps, and the like. The electrode 512 and/or the tip electrode 516 may allow the physician to measure the electrical activity of the tissue region (e.g., the lack of near-field electrical activity may indicate ablated tissue, whereas the presence of near-field electrical activity may indicate live tissue). In certain instances, the tip electrode 516 may include a hole (e.g., as shown in FIGS. 7-8) centrally a distal end thereof for interfacing with a guide wire or for contrast to be ejected therethrough. In addition, the tip electrode 516 may be collapsible (e.g., similar to an accordion) after entering into the tissue region. The tip electrode 516 may stabilize the apparatus 500 within the tissue region, and collapse if the balloon structure 504 is moved more distally within the tissue region. Collapsing the tip electrode 516 may facilitate positioning of the balloon structure 504 without increasing the pressure within the tissue region. In certain instances, the tip electrode 516 may be a mesh structure (e.g., formed from Nitinol) that may collapse and disperse the electrical energy over surface area of the mesh.

Additionally or alternatively, the apparatus 500 may include pacing electrodes 520, 522. The pacing electrodes 520, 522 may be arranged within the balloon structure 504. In certain instances, the pacing electrodes 520, 522 are arranged within the second portion 508 of the balloon structure 504. The pacing electrodes 520, 522 may be electrically coupled to a mapping signal processor such that electrical events in myocardial tissue can be sensed for the generation of electrograms, monophasic action potentials (MAPs), isochronal electrical activity maps, and the like. The pacing electrodes 520, 522 may allow the physician to measure the electrical activity of the tissue region (e.g., the lack of near-field electrical activity may indicate ablated tissue, whereas the presence of near-field electrical activity may indicate live tissue). The ablation energy applied via the electrode 512 may be altered based on the electrical activity measured by the pacing electrodes 520, 522, used to determine a target location for the ablation therapy.

The illustrative components shown in FIG. 5 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 5 may be, in embodiments, integrated with various other components depicted therein (and/or components not illustrated), all of which are considered to be within the ambit of the disclosed subject matter. For example, the pacing electrodes 520, 522 may be used in connection with apparatus 300 and apparatus 400.

Figure 6:
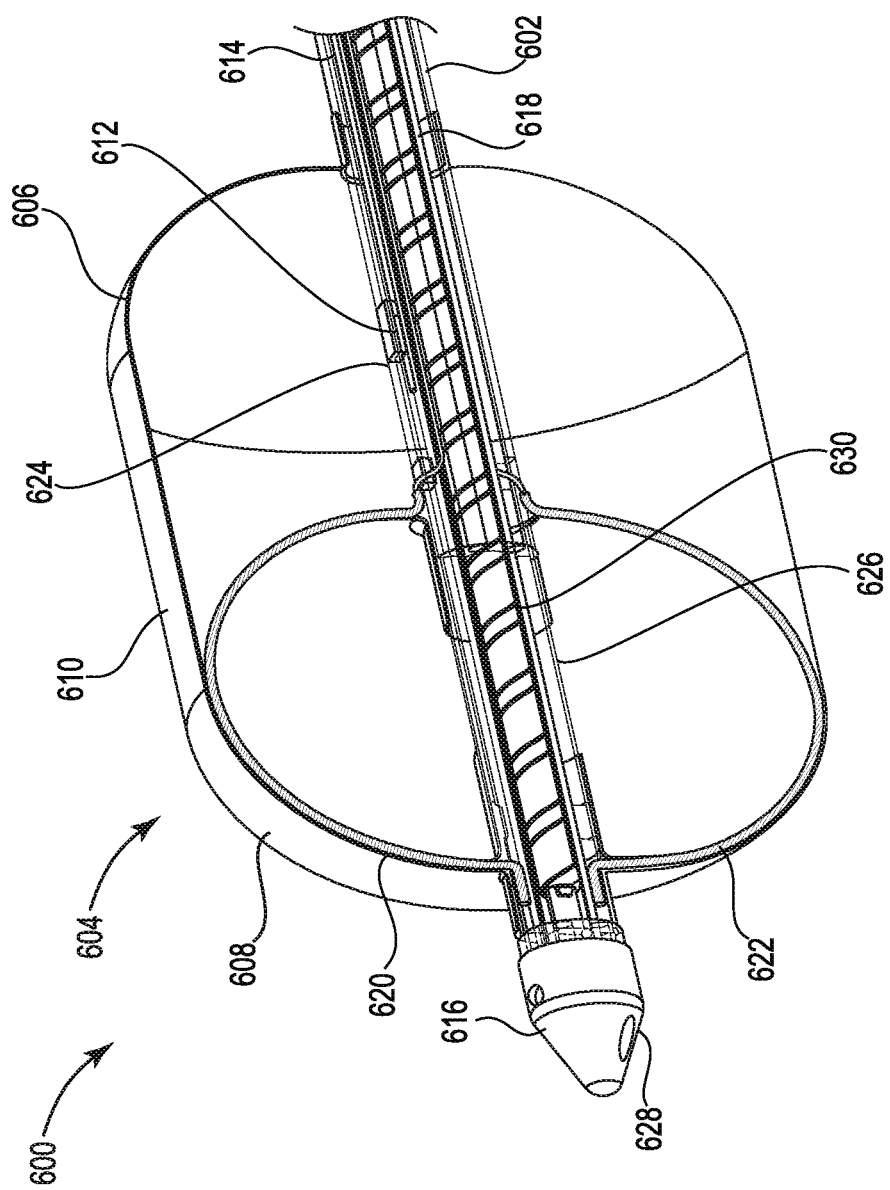
FIG. 6 shows a partial cross-sectional illustration of another exemplary apparatus for applying ablation therapy to a tissue region in accordance with embodiments of the disclosure.

FIG. 6 is a diagram illustrating a partial cross-section of another apparatus 600 for applying ablation therapy to a tissue region, in accordance with embodiments of the disclosure. The apparatus 600 includes a catheter having an elongate body 602. The apparatus 600 also may include a balloon structure 604 arranged at or near a distal portion of the elongate body 602. The balloon structure 604 may be configured to inflate in response to a liquid or inflation medium being provided thereto. In addition, the balloon structure 604 may include a first portion 606 and a second portion 608. In certain instances, the first portion 606 of the balloon structure 604 may be configured to permeate a liquid therethrough (in response to inflation of the balloon structure 604) and the second portion 608 of the balloon structure 604 may be to anchor the elongate body 602 at the tissue region.

The balloon structure 604 may be positioned at or within the tissue region for ablation. In certain instances, the tissue region may be a vessel such as a pulmonary vein or a renal vein. The balloon structure 604 may be configured to deploy within the vessel such that section 610 contacts the vessel wall. The first portion 606 may permeate the liquid to the tissue region (e.g., the vessel wall). The liquid may include an anti-stenotic agent that mitigates against stenosis within the vessel. In addition, the second portion 608 may anchor the elongate body 602 within the vessel.

In certain instances, the elongate body 602 includes a first opening 624 arranged within the first portion 606 (or chamber) and the elongate body 602 includes a second opening 626 arranged within the second portion 608 (or chamber). The first portion 606 (or chamber) is configured to elute a liquid therethrough in response to influx of the liquid into the first portion 606 (or chamber) through the first opening 624. In addition, the second portion 608 may be configured to expand and anchor the elongate body 602 at the tissue region in response to influx of a liquid into the second portion 608 (or chamber) through the second opening 626. The liquid eluted through the first portion 606 may be configured to mitigate against stenosis at the tissue region.

In certain instances, the apparatus 600 may also include an electrode 612, arranged within a lumen of the elongate body 602, that is configured to deliver energy to a tissue region. In certain instances, the electrode 612 may be arranged within the first portion 606 and configured to delivery energy in response to a direct current applied thereto. The ablation energy from the electrode 612 may be applied through an external surface of the first portion 606 of the balloon structure 604 by an electric field generated by an external source/controller and transferred through a wire 614 within the elongate body 602. The apparatus 600 may also include a tip electrode 616 that is configured to form a ground or a closed-loop with the electrode 612. The tip electrode 616 may be coupled to the external source/controller via a wire 618 arranged within the elongate body 602. In certain instances and as noted above, the electric field may be generated by applying direct current to the electrode 612. The use of direct current may cause apoptotic cell death to the tissue receiving the ablation energy. The direct current may form pores in the cells of the tissue region such that are irreversible (e.g., the pores do not close). The balloon structure 604 being in contact with the tissue may provide controlled and direct ablation of a target area while mitigating against down-stream proliferation of the ablation energy. In addition, the apparatus 600 may include a contrast port 628 arranged with the tip electrode 616. The contrast port 628 may be configured to eject contrast therethrough to assist in visualization of the apparatus 600 prior to and during ablation. The contrast port 628 may be off-set from a central axis of the elongate body 602. In certain instances, the tip electrode 616 may include multiple off-set contrast ports 628 to facilitate guidance into multiple side branch areas.

The electric energy can be transmitted to the tissue region (e.g., the vessel wall) via the liquid that permeates through the first portion 606 of the balloon structure 604. The electric field may modulate the activity along neural fibers within the wall of the tissue by at least partially causing apoptotic cell death to the tissue receiving the ablation energy. In certain instances while the electric field for ablation is being applied, transmission of the liquid from the first portion 606 of the balloon structure 604 to the tissue can be continued. The ablation process applied via the electrode 612 may be performed simultaneously and concurrently with the delivery of an antimitotic pharmacological agent as the liquid (or a saline, a contrast agent, an anti-stenotic agent, or a combination thereof) to the tissue receiving the ablation energy or the ablation process can be performed sequentially with the delivery of the liquid.

The apparatus 600 may include pacing electrodes 620, 622 arranged within the balloon structure 604. The pacing electrodes 620, 622 may be electrically coupled to a mapping signal processor such that electrical events in myocardial tissue can be sensed for the generation of electrograms, monophasic action potentials (MAPs), isochronal electrical activity maps, and the like. The pacing electrodes 620, 622 may allow the physician to measure the electrical activity of the tissue region (e.g., the lack of near-field electrical activity may indicate ablated tissue, whereas the presence of near-field electrical activity may indicate live tissue) and determine a target location for the ablation therapy.

In certain instances, the apparatus 600 may include a steering mechanism 630. The steering mechanism 630 may be configured to direct the balloon structure 604, the elongate body 602, or both the balloon structure 604, and the elongate body 602. As shown in FIG. 6, the steering mechanism 630 is arranged centrally within the elongate body 602. The steering mechanism 630 may direct the balloon structure 604 and/or the elongate body 602 in multiple directions based on a force applied thereto. The steering mechanism 630 may be a wire that is coupled to a catheter handle (e.g., as shown in FIG. 1).

FIG. 7 is a diagram illustrating a partial cross-section of another apparatus 700 for applying ablation therapy to a tissue region and having a steering mechanism, in accordance with embodiments of the disclosure. The apparatus 700 includes a catheter having an elongate body 702 and a balloon structure 704 attached to the elongate body 702. The balloon structure 704 may be configured to inflate in response to a liquid or inflation medium. In addition, the balloon structure 704 may include a first portion 706 and a second portion 708. In certain instances, the first portion 706 of the balloon structure 704 may be configured to permeate a liquid therethrough (in response to inflation of the balloon structure 704) and the second portion 708 of the balloon structure 704 may be to anchor the elongate body 702 at the tissue region.

The balloon structure 704 may be positioned at or within the tissue region for ablation. In certain instances, the tissue region may be a vessel such as a pulmonary vein or a renal vein. The first portion 706 may permeate the liquid to the tissue region (e.g., the vessel wall). The liquid may include an anti-stenotic agent that mitigates against stenosis within the vessel. In addition, the second portion 708 may anchor the elongate body 702 within the vessel.

Electric energy can be transmitted to the tissue region (e.g., the vessel wall) via the liquid that permeates through the first portion 706 of the balloon structure 704. The electric field may modulate the activity along neural fibers within the wall of the tissue by at least partially causing apoptotic cell death to the tissue receiving the ablation energy. In certain instances while the electric field for ablation is being applied, transmission of the liquid the first portion 706 of the balloon structure 704 to the tissue can be continued. The ablation process applied via an electrode 712 may be performed simultaneously and concurrently with the delivery of an antimitotic pharmacological agent as the liquid (or a saline, a contrast agent, an antimitotic pharmacological agent or combination thereof) to the tissue receiving the ablation energy or the ablation process can be performed sequentially with the delivery of the liquid. The electrode 712, arranged with the elongate body 702 within the first portion 704, is configured to deliver energy to a tissue region. The ablation energy from the electrode 712 may be applied through an external surface of the first portion 706 of the balloon structure 704 by an electric field generated by an external source/controller and transferred through a wire 714 within the elongate body 702. In certain instances and as noted above, the electric field may be generated by applying direct current to the electrode 712. The use of direct current may cause apoptotic cell death to the tissue receiving the ablation energy. The direct current may form pores in the cells of the tissue region such that are irreversible (e.g., the pores do not close). The balloon structure 704 being in contact with the tissue may provide controlled and direct ablation of a target area while mitigating against downstream proliferation of the ablation energy.

A tip electrode 716 may also be used to form a ground or a closed-loop with the electrode 712. The tip electrode 716 may also be coupled to the external source/controller. In addition, the apparatus 700 may include a contrast port 710 arranged with the tip electrode 716. The contrast port 710 may be configured to eject contrast therethrough to assist in visualization of the apparatus 700 prior to and during ablation. The contrast port 710 may be arranged at a distal end of the tip electrode 716.

Pacing electrodes 720, 722 arranged within the balloon structure 704 may be configured to determine electrical activity of the tissue region. The pacing electrodes 720, 722 may be used prior to ablation to estimate an extent tissue damage. In addition, the pacing electrodes 720, 722 may be used after the ablation to determine the extent of the ablation. The pacing electrodes 720, 722 may be electrically coupled to a mapping signal processor such that electrical events in myocardial tissue can be sensed for the generation of electrograms, monophasic action potentials (MAPs), isochronal electrical activity maps, and the like. The pacing electrodes 720, 722 may allow the physician to measure the electrical activity of the tissue region (e.g., the lack of near-field electrical activity may indicate ablated tissue, whereas the presence of near-field electrical activity may indicate live tissue) and determine a target location for the ablation therapy.

In certain instances, the apparatus 700 may be steerable and include a first steering wire 724 and a second steering wire 726. The first steering wire 724 and the second steering wire 726 may be configured to direct the balloon structure 704, the elongate body 702, or both the balloon structure 704 and the elongate body 702. The first steering wire 724 and the second steering wire 726 are arranged within the elongate body 702 on either side of a central lumen 728. As described in detail above, the central lumen 728 may include portions that carry liquid to each of the first portion 706 and the second portion 708. The first steering wire 724 and the second steering wire 726 may direct the balloon structure 704 and/or the elongate body 702 in multiple directions based on a force applied thereto. The first steering wire 724 and the second steering wire 726 may be coupled to a catheter handle (e.g., as shown in FIG. 1).

In certain instances, one or both of the first portion 706 and the second portion 708 may include a stent support structure 730. The stent support structure 730 may enhance the structural stability of one or both of the first portion 706 and the second portion 708.

FIG. 8 is a diagram illustrating a partial cross-section of another apparatus 800 for applying ablation therapy to a tissue region and having a visualization element, in accordance with embodiments of the disclosure. The apparatus 800 includes a catheter having an elongate body 802 and a balloon structure 804 attached to the elongate body 802. The balloon structure 804 may include a first portion 806 and a second portion 808. In certain instances, the first portion 806 of the balloon structure 804 may be configured to permeate a liquid therethrough and the second portion 808 of the balloon structure 804 may be to anchor the elongate body 802 at the tissue region in response to inflation of the balloon structure 804). The balloon structure 804 may be positioned at or within the tissue region for ablation. In certain instances, the tissue region may be a vessel such as a pulmonary vein or a renal vein. The first portion 806 may permeate the liquid to the tissue region (e.g., the vessel wall). The liquid may include an anti-stenotic agent that mitigates against stenosis within the vessel. In addition, the second portion 808 may anchor the elongate body 802 within the vessel.

Electric energy can be transmitted to the tissue region (e.g., the vessel wall) via the liquid that permeates through the first portion 806 of the balloon structure 804. The electric field may modulate the activity along neural fibers within the wall of the tissue by at least partially causing apoptotic cell death to the tissue receiving the ablation energy. In certain instances while the electric field for ablation is being applied, transmission of the liquid the first portion 806 of the balloon structure 804 to the tissue can be continued. The ablation process applied via an electrode 812 may be performed simultaneously and concurrently with the delivery of an antimitotic pharmacological agent as the liquid (or a saline, a contrast agent, an antimitotic pharmacological agent, or combination thereof) to the tissue receiving the ablation energy or the ablation process can be performed sequentially with the delivery of the liquid. The ablation energy from the electrode 812 may be applied through an external surface of the first portion 806 of the balloon structure 804 by an electric field generated by an external source/controller and transferred through a wire 814 within the elongate body 802.

A tip portion 810 of the apparatus 800 may be configured to facilitate position of the balloon structure 804 at the tissue region. The tip portion 810 may include a central aperture 816 that may assist in passing the elongate body 802 and the balloon structure 804 through a puncture in an atrial septum to access the left atrium of a patient's heart. The central aperture 816 may pass a guidewire therethrough to assist in positioning of the tip portion 810 at the septum. Subsequently, a puncture tool may be arranged through the elongate body 802 and through the central aperture 816 to puncture the septum. The central aperture 816 may also be configured to eject contrast therethrough to assist in visualization of the apparatus 800 prior to and during ablation.

A visualization element 824 may also be used to assist in visualization. The visualization element 824 may include a camera and a light source (e.g., a light emitting diode (LED)). The visualization element 824 may be arranged with the elongate body 802 and configured to view and provide an image of video to a physician operating the apparatus 800. After positioning of the balloon structure 804 at the tissue region such as within the pulmonary vein (as shown in FIG. 2), the balloon structure 804 may be expanded. The inflation of the balloon structure 804 may cause the outer surface of the balloon structure 804 to contact an inner wall of the vessel. More specifically, the second portion 808 of the balloon structure 804 may anchor the elongate body 802 within the vessel. The visualization element 824 may be used to observe blood flow through the tissue area. In certain instances, the second portion 808 may block blood from through the tissue area such that the liquid eluted from the first portion 806 is directly applied to the tissue area. Blocking blood flow may mitigate against the liquid (e.g., anti-stenotic pharmaceutical agent) being carried from the tissue region. The anti-stenotic pharmaceutical liquid that may contact the tissue region (the inner wall of the vessel) and mitigate against stenosis formation that may result from the application of ablation energy applied via the electrode 812.

Pacing electrodes 820, 822 arranged within the balloon structure 804 may be configured to determine electrical activity of the tissue region. The pacing electrodes 820, 822 may be used prior to ablation to estimate an extent tissue damage. In addition, the pacing electrodes 820, 822 may be used after the ablation to determine the extent of the ablation. The pacing electrodes 820, 822 may be electrically coupled to a mapping signal processor such that electrical events in myocardial tissue can be sensed for the generation of electrograms, monophasic action potentials (MAPs), isochronal electrical activity maps, and the like. The pacing electrodes 820, 822 may allow the physician to measure the electrical activity of the tissue region (e.g., the lack of near-field electrical activity may indicate ablated tissue, whereas the presence of near-field electrical activity may indicate live tissue) and determine a target location for the ablation therapy.

The illustrative components shown in FIGS. 6-8 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 6-8 may be, in embodiments, integrated with various other components depicted therein (and/or components not illustrated), all of which are considered to be within the ambit of the disclosed subject matter. For example, the pacing electrodes 520, 522 may be used in connection with apparatus 300 and apparatus 400. In addition, apparatus 300 and apparatus 400 may include steering mechanisms and/or visualization elements as described with reference to FIGS. 6-8. Further, the tip sections of the apparatuses 600-800 may be collapsible as described above with reference to FIG. 5.

FIG. 9A is a diagram illustrating a partial cross-section of another apparatus 900 for applying stenosis prevention to a tissue region and having a first multiple chamber configuration, in accordance with embodiments of the disclosure. The apparatus 900 may include an elongate body 902 and a balloon structure 904. In the first multiple chamber configuration shown in FIG. 9A, the balloon structure 904 may include two chambers 906, 908 that are configured to anchor the elongate body 902 at the tissue region. The chambers 906, 908 may be impermeable to liquid applied to inflate the balloon structure 904. The balloon structure 904 may also include a third chamber 910 that is configured to permeate a liquid therethrough. The liquid may be an anti-stenotic agent and may prevent stenosis formation at the tissue region.

FIG. 9B is a diagram illustrating the apparatus 900 for applying stenosis prevention depicted FIG. 9A and having a second multiple chamber configuration, in accordance with embodiments of the disclosure. In the second multiple chamber configuration shown in FIG. 9B, the balloon structure 904 may include two chambers 906, 908 that are configured to anchor the elongate body 902 at the tissue region. The chambers 906, 908 may be impermeable to liquid applied to inflate the balloon structure 904. The third chamber 910 that is configured to permeate a liquid therethrough. The liquid may be an anti-stenotic agent and may prevent stenosis formation at the tissue region. The chambers 906, 908 are smaller than the first configuration chambers 906, 908 to allow for a larger third chamber 910.

FIG. 9C is a diagram illustrating the apparatus 900 for applying stenosis prevention depicted in FIGS. 9A-B and having a third multiple chamber configuration, in accordance with embodiments of the disclosure. In the third multiple chamber configuration shown in FIG. 9B, the balloon structure 904 may include three chambers 906, 908, 912 that are configured to anchor the elongate body 902 at the tissue region. The chambers 906, 908, 912 may be impermeable to liquid applied to inflate the balloon structure 904. The apparatus includes the third chamber 910 configured to permeate a liquid therethrough and a fourth chamber 914 that is also configured to permeate a liquid therethrough. The liquid may be an anti-stenotic agent and may prevent stenosis formation at the tissue region. In the third configuration, the apparatus 900 includes two regions of permeability 916, 918 through which the liquid (e.g., the anti-stenotic agent) may permeate. Any of the first, second, and third configurations of the apparatus 900 may also include electrodes that are configured to apply ablation energy, as described in detail above. The electrodes may be arranged within the chambers that permeate the liquid.

Figure 10:
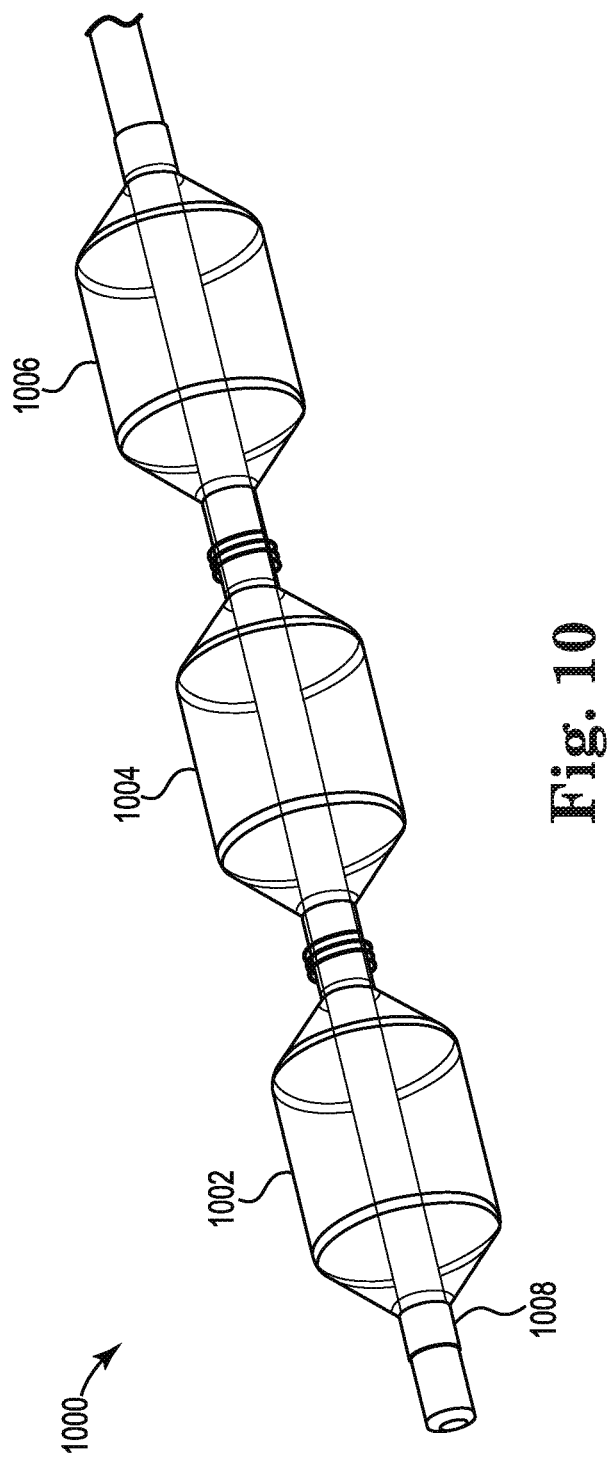
FIG. 10 shows another exemplary apparatus for applying stenosis prevention to a tissue region having a multiple chamber configuration in accordance with embodiments of the disclosure.

FIG. 10 is a diagram illustrating another apparatus 1000 for applying stenosis prevention to a tissue region and having a multiple chamber configuration, in accordance with embodiments of the disclosure. The apparatus 1000 includes three chambers 1002, 1004, 1006 along an elongate body 1008 of a catheter. Each of the three chambers 1002, 1004, 1006 may be configured to permeate an anti-stenotic liquid therethrough. In certain instances, the entirety of the three chambers 1002, 1004, 1006 may be permeable to the liquid, and in other instances, only a portion of the three chambers 1002, 1004, 1006 may be permeable to the liquid. The permeability (or lack thereof) may differ between the three chambers 1002, 1004, 1006. Any of the three chambers 1002, 1004, 1006 may also include electrodes that are configured to apply ablation energy, as described in detail above.

Figure 11A:
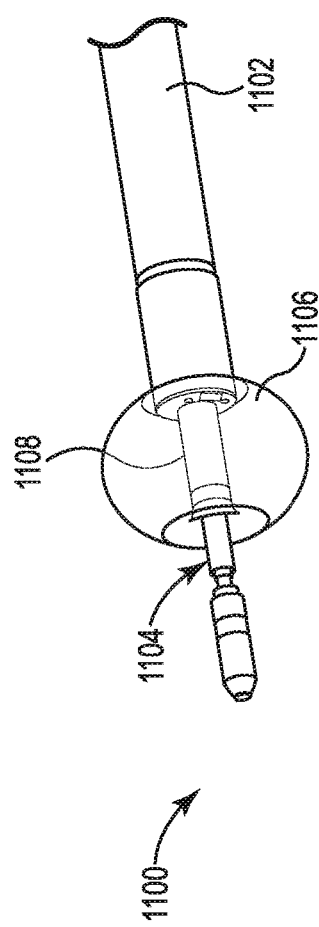
FIG. 11A shows another exemplary apparatus for applying ablation therapy to a tissue region having a telescoping balloon in a first configuration in accordance with embodiments of the disclosure.

FIG. 11A is a diagram illustrating another apparatus 1100 for applying ablation therapy to a tissue region and having a telescoping balloon in a first configuration, in accordance with embodiments of the disclosure. The apparatus 1100 may include a catheter having an elongate body 1102 and a balloon structure 1104 attached to the elongate body 1102. The balloon structure 1104 may be configured to telescope from the elongate body 1102 prior to inflation thereof. As shown in FIG. 11A, the balloon structure 1104 is arranged in a first configuration prior to telescoping from the elongate body 1102.

A second balloon structure 1106 may be arranged with the elongate body 1102. The second balloon structure 1106 may house a visualization element 1108. The visualization element 1108 may also be used to assist in visualization during the application of ablation therapy. The visualization element 1108 may include a camera and a light source (e.g., a light emitting diode (LED)). The visualization element 1108 may be configured to view and provide an image of video to a physician operating the apparatus 1100.

In the first configuration, the elongate body 1102 and the catheter may be navigated to a tissue region. More specifically, the elongate body 1102 and the catheter may be navigated within the patient's heart. After navigating to the patient's heart (e.g. as described above with reference to FIG. 2), the balloon structure 1104 may be positioned at the tissue region. In certain instances, the tissue region may be a vessel such as a pulmonary vein. In these such instances, the balloon structure 1104 is arranged within the vessel.

Figure 11B:
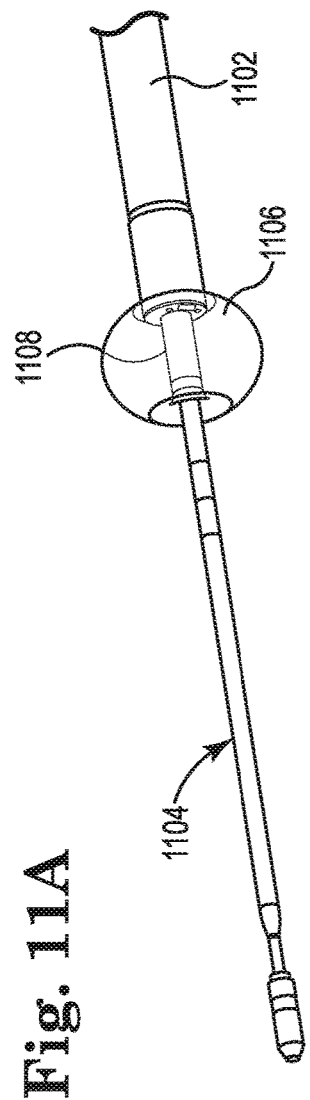
FIG. 11B shows the apparatus for applying ablation therapy, as shown in FIG. 11A, in a second configuration in accordance with embodiments of the disclosure.

FIG. 11B is a diagram illustrating the apparatus 1100 for applying ablation therapy depicted in FIG. 11A in a second configuration, in accordance with embodiments of the disclosure. In the second configuration, the balloon structure 1104 has been telescoped from the elongate body 1102 and has not yet been inflated. The positioning of the balloon structure 1104 at the tissue region (within the blood vessel) may occur during transition of the balloon structure 1104 between the first configuration and the second configuration, or after transition of the balloon structure 1104 to the second configuration. The balloon structure 1104 may include a section arranged within the elongate body 1102 that connects to a catheter handle. This section may be configured to slide within the elongate body 1102 to telescope the balloon structure 1104 therefrom.

Figure 11C:
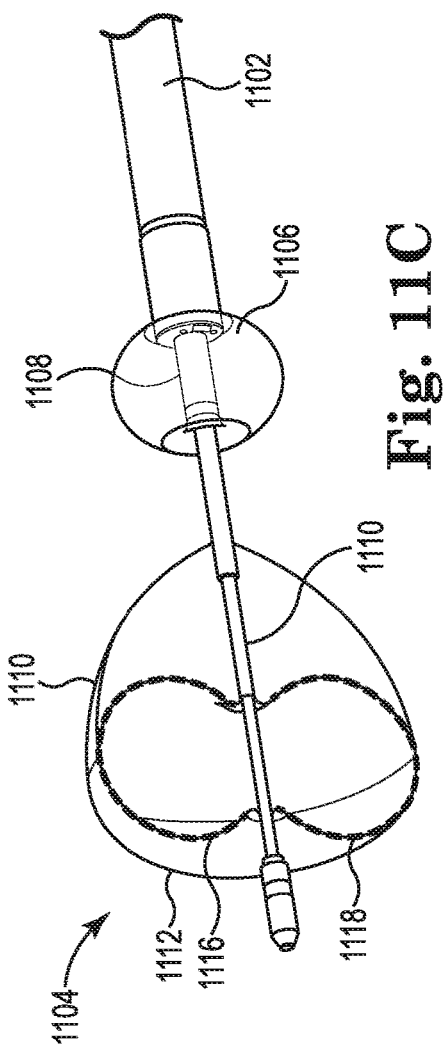
FIG. 11C shows the apparatus for applying ablation therapy, as shown in FIGS. 11A-B in a third configuration in accordance with embodiments of the disclosure.

FIG. 11C is a diagram illustrating the apparatus 1100 for applying ablation therapy depicted in FIGS. 11A-B in a third configuration, in accordance with embodiments of the disclosure. In the third configuration, the balloon structure 1104 has been inflated. The balloon structure 1104 may include a first portion 1110 and a second portion 1112. In certain instances, the first portion 1110 of the balloon structure 1104 may be configured to permeate a liquid therethrough and the second portion 1112 of the balloon structure 1104 may be to anchor the elongate body 1102 at the tissue region in response to inflation of the balloon structure 1104). Thus, the first portion 1110 of the balloon structure 1104 may include a first permeability, and the second portion 1112 of the balloon structure 1104 may include a second permeability, with the first permeability being greater than the second permeability. The balloon structure 1104 may be positioned at or within the tissue region for ablation. In certain instances, the tissue region may be a vessel such as a pulmonary vein or a renal vein. The first portion 1110 may permeate the liquid to the tissue region (e.g., the vessel wall). The liquid may include an anti-stenotic agent that mitigates against stenosis within the vessel. In addition, the second portion 1112 may anchor the elongate body 1102 within the vessel.

An ablation process applied via an electrode 1114 may be performed simultaneously and concurrently with the delivery of an antimitotic pharmacological agent as the liquid (or a saline, a contrast agent, an antimitotic pharmacological agent, or combination thereof) to the tissue receiving the ablation energy or the ablation process can be performed sequentially with the delivery of the liquid. Electric energy can be transmitted to the tissue region (e.g., the vessel wall) via the liquid that permeates through the first portion 1110 of the balloon structure 1104. The electric field may modulate the activity along neural fibers within the wall of the tissue by at least partially causing apoptotic cell death to the tissue receiving the ablation energy. In certain instances, while the electric field for ablation is being applied, transmission of the liquid the first portion 1110 of the balloon structure 1104 to the tissue can be continued. The ablation energy from the electrode 1114 may be applied through an external surface of the first portion 1110 of the balloon structure 1104 by an electric field generated by an external source/controller and transferred coupled to the electrode 1114.

After positioning of the balloon structure 1104 at the tissue region such as within the pulmonary vein (as shown in FIG. 2), the inflation of the balloon structure 1104 may cause the outer surface of the balloon structure 1104 to contact an inner wall of the vessel such. More specifically, the second portion 1112 of the balloon structure 1104 may anchor the elongate body 1102 within the vessel. The visualization element 1108 may be used to observe blood flow through the tissue area. In certain instances, the second portion 1112 may block blood from through the tissue area such that the liquid eluted from the first portion 1110 is directly applied to the tissue area. Blocking blood flow may mitigate against the liquid (e.g., anti-stenotic pharmaceutical agent) being carried from the tissue region. The anti-stenotic pharmaceutical liquid that may contact the tissue region (the inner wall of the vessel) and mitigate against stenosis formation that may result from the application of ablation energy applied via the electrode 1114.

In addition, the balloon structure 1104 may include pacing electrodes 1116, 1118 arranged therein. The pacing electrodes 1116, 1118 may be configured to determine electrical activity of the tissue region. The pacing electrodes 1116, 1118 may be used prior to ablation to estimate an extent tissue damage. In addition, the pacing electrodes 1116, 1118 may be used after the ablation to determine the extent of the ablation. The pacing electrodes 1116, 1118 may be electrically coupled to a mapping signal processor such that electrical events in myocardial tissue can be sensed for the generation of electrograms, monophasic action potentials (MAPs), isochronal electrical activity maps, and the like. The pacing electrodes 1116, 1118 may allow the physician to measure the electrical activity of the tissue region (e.g., the lack of near-field electrical activity may indicate ablated tissue, whereas the presence of near-field electrical activity may indicate live tissue).

In certain instances, when balloon structure 1104 is deployed (e.g., inside the pulmonary vein) the balloon structure 1104 may be positioned therein as distally as possible toward the bifurcation where the pulmonary vein splits. At this point, the second portion 1112 may be inflated first to anchor the elongate body 1102 therein. Inflation of the second portion 1112 may stop blood flow to the left atrium, which may be verified by the visualization element 1108. Subsequently, the pacing electrodes 1116, 1118 may measure the electrical activity of the pulmonary vein. The measurement by the pacing electrodes 1116, 1118 may provide a baseline for the ablation therapy. Ablation therapy may be applied via the electrode 1114, based on the measurement of the pacing electrodes 1116, 1118, along with release of an anti-stenotic via the liquid permeated through the first portion 1110. In certain instances, the liquid may be permeate through the first portion 1110 prior to the application of ablation therapy. The visualization element 1108 and/or an ultrasound may verify that the liquid (e.g., saline and the anti-stenotic) is flowing to the vessel wall prior to the application of ablation via the electrode 1114.

After ablation is applied, the pacing electrodes 1116, 1118 may be used again to measure the electrical activity. If the desired level of ablation has occurred based on the reading of the balloon structure 1104 may be deflated and removed from the pulmonary vein. In certain instances, the balloon structure 1104 may be moved along the pulmonary vein to a second ablation site. The second portion 1112 may remain inflated during repositioning of the balloon structure 1104. The electrical activity of the second ablation may be measured by the pacing electrodes 1116, 1118, and the liquid permeation and ablation may occur. This process may be repeated until the desired level of ablation is achieved. The movement to the second ablation site (e.g., 5 mm) may be determined based on a change in the electrical activity measured by the pacing electrodes 1116, 1118. In addition the electrode 1114 may apply electrical energy via direct current applied thereto at various pulse width patterns and amplitudes (e.g., 1-30 microsecond pulses at 1000-3000 volts). For further detail regarding the ablation procedure, including mapping use the pacing electrodes 1116, 1118, reference may be made to the FIG. 1 and the related discussion.

The illustrative components shown in FIGS. 11A-C are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 11A-C may be, in embodiments, integrated with various other components depicted therein (and/or components not illustrated), all of which are considered to be within the ambit of the disclosed subject matter.

Figure 12:
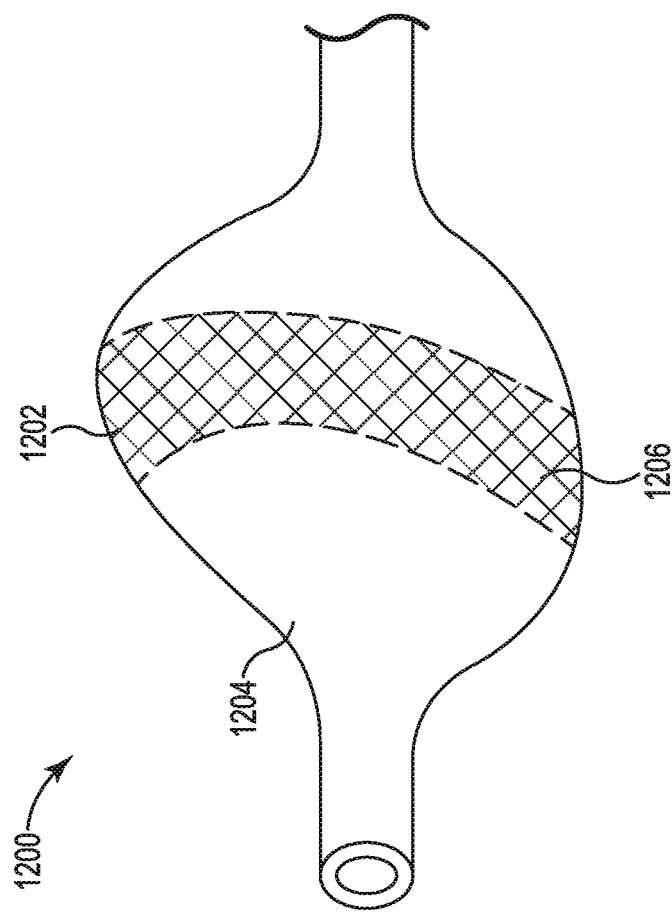
FIG. 12 shows an exemplary balloon structure for applying stenosis prevention to a tissue region having a plurality of nanostructures in accordance with embodiments of the disclosure.

FIG. 12 is a diagram illustrating a balloon structure 1200 for applying stenosis prevention to a tissue region and having a plurality of nanostructures, in accordance with embodiments of the disclosure. The balloon structure 1200 may include a permeability portion 1202 and non-permeability portion 1204. The permeability portion 1202 may include a plurality of nanostructures 1206. In certain instances, the nanostructures 1206 may be hollow fibers that act as a core material to contain a liquid, such as an anti-stenotic drug. In other instances, the plurality of nanostructures 1206 may contain a liquid, such as an anti-stenotic drug, in gaps between the plurality of nanostructures 1206. The plurality of nanostructures 1206 in either instance may form a cross-hatched network within the permeability portion 1202.

The plurality of nanostructures 1206 may be arranged on the balloon structure 1200 by fiber deposition, fiber sintering (thermal or chemical), hydrophilic or hydrophobic coating, or other similar processes. In addition, the permeability portion 1202 may include multiple layers such that one layer may include the plurality of nanostructures 1206, and another layer is arranged thereon to mitigate against release of the liquid from the plurality of nanostructures 1206. The liquid may release from the plurality of nanostructures 1206, with or within the layer arranged thereon, in response to inflation of the balloon structure 1200. The liquid, such as the anti-stenotic drug, may be delivered to a tissue region by diffusion into the tissue, or may be driven by iontophoresis by an electrical force originating from an electrode (not shown) arranged within the balloon structure 1200. In other instances, the plurality of nanostructures 1206 may be replaced with a coating on the balloon structure 1200 of the anti-stenotic drug. This may include combing the anti-stenotic drug with water or saline (e.g., 4.86% 80/20 ptx/ ATBC in 40/40/20 EtOH/Acetone/water). In certain instances, the balloon structure 1200 may have multiple layers. One or more anti-stenotic drugs, saline, contrast agents, pharmacological agents, or combinations thereof may be impregnated within the different layers of the balloon structure 1200. Sequential delivery of the anti-stenotic stenotic drugs, saline, contrast agents, pharmacological agents, or combinations thereof may be delivered via the different layers of the balloon structure 1200. In addition, the balloon structure 1200 may have different layers in different portions thereof for sequential delivery of the anti-stenotic drugs, saline, contrast agents, pharmacological agents, or combinations thereof.

The illustrative components shown in FIG. 12 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 12 may be, in embodiments, integrated with various other components depicted therein (and/or components not illustrated), all of which are considered to be within the ambit of the disclosed subject matter. For example, the nanostructures 1206 may be used in connection with any of the balloon structures discussed herein.

Figure 13:
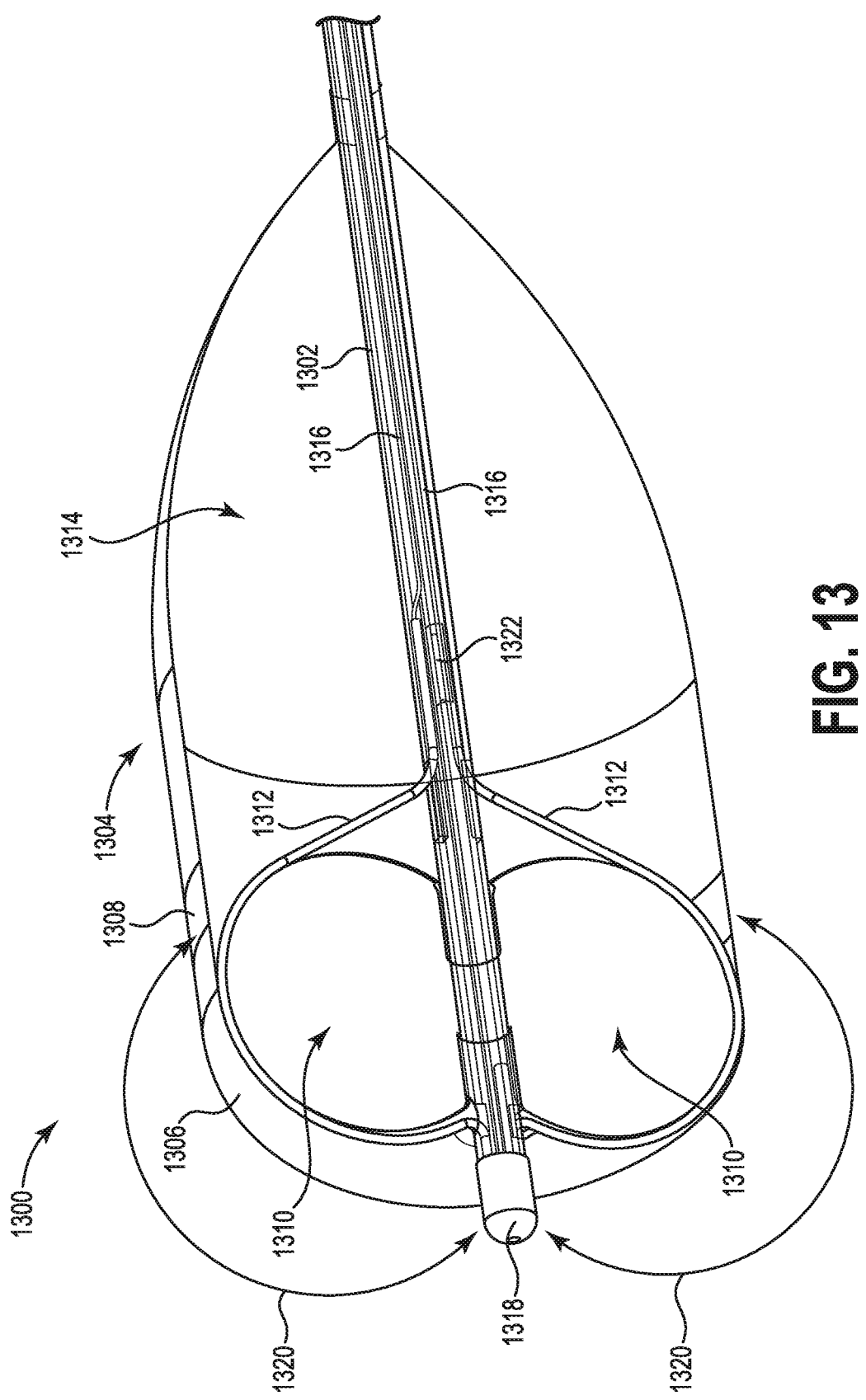
FIG. 13 a diagram illustrating a partial cross-section of another apparatus for applying ablation therapy to a tissue region, in accordance with embodiments of the disclosure.

FIG. 13 is a diagram illustrating a partial cross-section of another apparatus 1300 for applying ablation therapy to a tissue region and having a steering mechanism, in accordance with embodiments of the disclosure. The apparatus 1300 includes a catheter having an elongate body 1302. In embodiments, the apparatus 1300 may also include a balloon structure 1304 arranged at or near a distal portion of the elongate body 1302.

According to embodiments, the balloon structure 1304 may include a surface formed of at least a first portion 1306 and a second portion 1308. In embodiments, the permeability of the first portion 1306 may be different than the permeability of the second portion 1308. The permeability of the first portion 1306 may be referred to as a first permeability and the permeability of the second portion 1308 may be referred to as a second permeability. In embodiments, the second permeability may be greater than the first permeability. For example, the second portion 1308 of the balloon structure 1304 may be configured to allow a liquid to permeate or elute therethrough (e.g., in response to inflation of the balloon structure 1304) and the permeability of the first portion 1306 may be zero (or approximately zero) such that liquid does not permeate or elute therethrough. In embodiments, the permeability of the second portion 1308 may be due to pores in the second portion 1308 that may be between approximately 1 millimeter and approximately 10 millimeters in diameter when the balloon structure 1304 is inflated. In embodiments, the permeability of the second portion 1308 may contribute to delivering ablation energy to target tissue, as discussed below.

In embodiments, the second portion 1308 may have a strip shape that circumferentially extends at least partially around the balloon structure 1304. Alternatively, the second portion 1308 may have other shapes including, for example, circles, ellipses, quadrilaterals, triangles, combinations of shapes, and/or the like.

In embodiments, the balloon structure 1304 may be positioned near a target tissue region for ablation. The tissue region may be a vessel such as a pulmonary vein, renal vein, portion of the liver, portion of the esophagus and/or other appendage. After positioning the balloon structure 1304 near a target tissue region, the balloon structure 1304 may be inflated. For example, the balloon structure 1304 may be configured to inflate in response to a liquid or inflation medium being provided thereto. In embodiments, the balloon structure 1304 may include a chamber 1310, which is configured to inflate in response to a liquid or inflation medium being provided thereto. Once inflated, the chamber 1310 may push electrodes 1312 towards the exterior of the apparatus 1300 in order to facilitate delivering ablative energy to a tissue region, as described in more detail below. Additionally or alternatively, the chamber 1310, once inflated, may facilitate anchoring the balloon structure 1304 to a tissue region.

Additionally or alternatively, the balloon structure 1304 may include a chamber 1314 that may also be inflated in response to receiving a liquid or other inflation medium. After being inflated, the second portion 1308 of the balloon structure 1304 may contact a target tissue region. In embodiments, the second portion 1308 may form part of the chamber 1314 (e.g., a wall of the chamber 1314) and/or the second portion 1308 and the chamber 1314 may be in fluid communication with one another. As such, once the chamber 1314 is inflated, the liquid and/or other inflation medium may permeate through the second portion 1308. In embodiments, a consistent supply of liquid and/or another inflation medium may be delivered to the chamber 1314 to substantially offset any liquid and/or other inflation medium that permeates through the second portion 1308.

According to embodiments, the apparatus 1300 may include one or more electrodes 1312 arranged within the balloon structure 1304. In embodiments, the electrodes 1312 may be used to delivery ablative energy to a tissue region. For example, an external source/controller may apply a voltage to the electrodes 1312 via one or more wires disposed in lumens 1316 positioned on one or more sides of a central lumen (not shown). In embodiments, direct-current (DC) voltages between approximately 1000 V to 5000 V may be used. In embodiments, higher voltages (e.g., between 3000V to 5000 V) may be used to treat a cancerous tumor and lower voltages (e.g., between 1000 V to 3000 V) may be used to ablate a tissue region. However, these are only examples and not meant to be limiting. In response to the voltage being applied to the electrodes 1312, an electric field may be generated between the electrodes 1312 and a second electrode having a ground electrical potential and/or lower electric potential than the electrodes 1312. The electric field generated between the electrodes 1312 and a second electrode elicits a current that passes through a tissue region. In embodiments, the current may be delivered via a liquid and/or other inflation medium of the chamber 1314, through the second portion 1308 (since the liquid and/or other inflation medium can permeate the second portion 1308), and to the tissue region (e.g., the vessel wall). The delivered current may modulate the activity along neural fibers within the wall of the tissue by at least partially causing apoptotic cell death to the tissue receiving the ablation energy. Additionally or alternatively, the electrodes 1312 may be grounded and/or held at a lower electric potential than the second electrode to facilitate current flowing from the second electrode to the electrodes 1312. As such, in embodiments, current may flow from the second electrode to the electrodes 1312 and/or vice versa. Additionally or alternatively, one or more metal portions of the elongate body 1302 may be used to generate the electric field used to ablate tissue.

According to embodiments, the majority of the current will not pass through the first portion 1306 of the balloon structure 1304 since the liquid and/or other inflation medium of the chamber 1314 cannot permeate the first portion 1306. Therefore, based on the position of the second portion 1308 relative to the tissue, the current produced by the electrodes 1312 may be applied to tissue in a controlled and localized manner.

In embodiments, a tip electrode 1318 may be used as the second electrode to form a ground and/or a closed-loop with the electrodes 1312. In embodiments where the tip electrode 1318 is used as the second electrode, a current may be generated between the electrodes 1312 and the tip electrode 1318 via the second portion 1308, as indicated by the arrows 1320. In embodiments, the tip electrode 1318 may also be coupled to the external source/controller.

According to embodiments, the electrodes 1312 may be configured to determine electrical activity of the tissue region. For example, the electrodes 1312 may be used prior to ablation to estimate an extent of tissue damage. Additionally or alternatively, the electrodes 1312 may be used after the ablation to determine the extent of the ablation. According to embodiments, the electrodes 1312 may be electrically coupled to a mapping signal processor such that electrical events in myocardial tissue can be sensed for the generation of electrograms, monophasic action potentials (MAPs), isochronal electrical activity maps, and the like. As such, the electrodes 1312 may allow the physician to measure the electrical activity of the tissue region (e.g., the lack of near-field electrical activity may indicate ablated tissue, whereas the presence of near-field electrical activity may indicate live tissue) and determine a target location for the ablation therapy.

In embodiments, the apparatus 1300 may be steerable and include one or more steering wires 1322. The steering wires 1322 may be configured to direct the balloon structure 1304, the elongate body 1302, or both. The steering wires 1322 may be arranged within a central lumen (not shown) of the elongate body 1302. The steering wires 1322 may direct the balloon structure 1304 and/or the elongate body 1302 in multiple directions based on a force applied thereto. The steering wires 1322 may be coupled to a catheter handle (e.g., as shown in FIG. 1). Additionally or alternatively, lumens 1316 disposed on one or more sides of the central lumen may be used to transport liquid to each of the chambers 1310, 1314.

The illustrative apparatus 1300 shown in FIG. 13 is not intended to suggest any limitation as to the scope of use or functionality of embodiments of the present disclosure. Neither should the illustrative apparatus 1300 be interpreted as having any dependency nor requirement related to any single component or combination of components illustrated therein. Additionally, various components depicted in FIG. 13 may be, in embodiments, integrated with various ones of the other components depicted therein (and/or components not illustrated), all of which are considered to be within the ambit of the present disclosure.

Figure 14A:
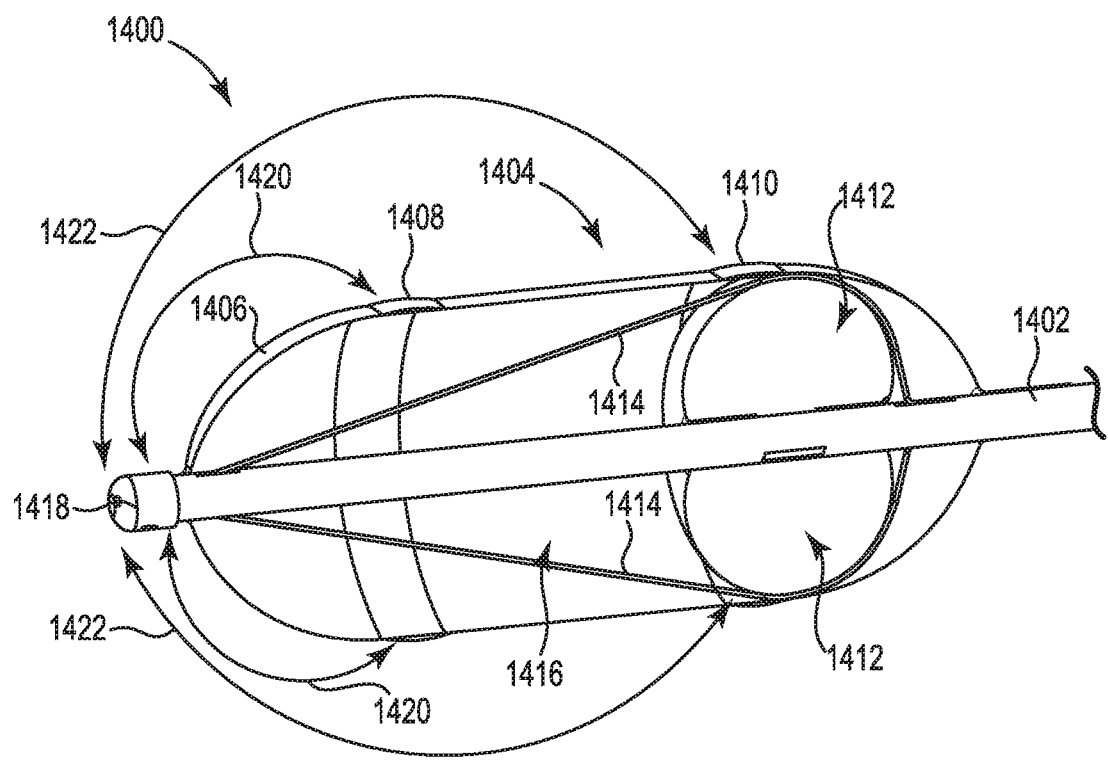
FIGS. 14A and 14B are diagrams illustrating partial cross-sections of another apparatus for applying ablation therapy to a tissue region, in accordance with embodiments of the disclosure.
Figure 14B:
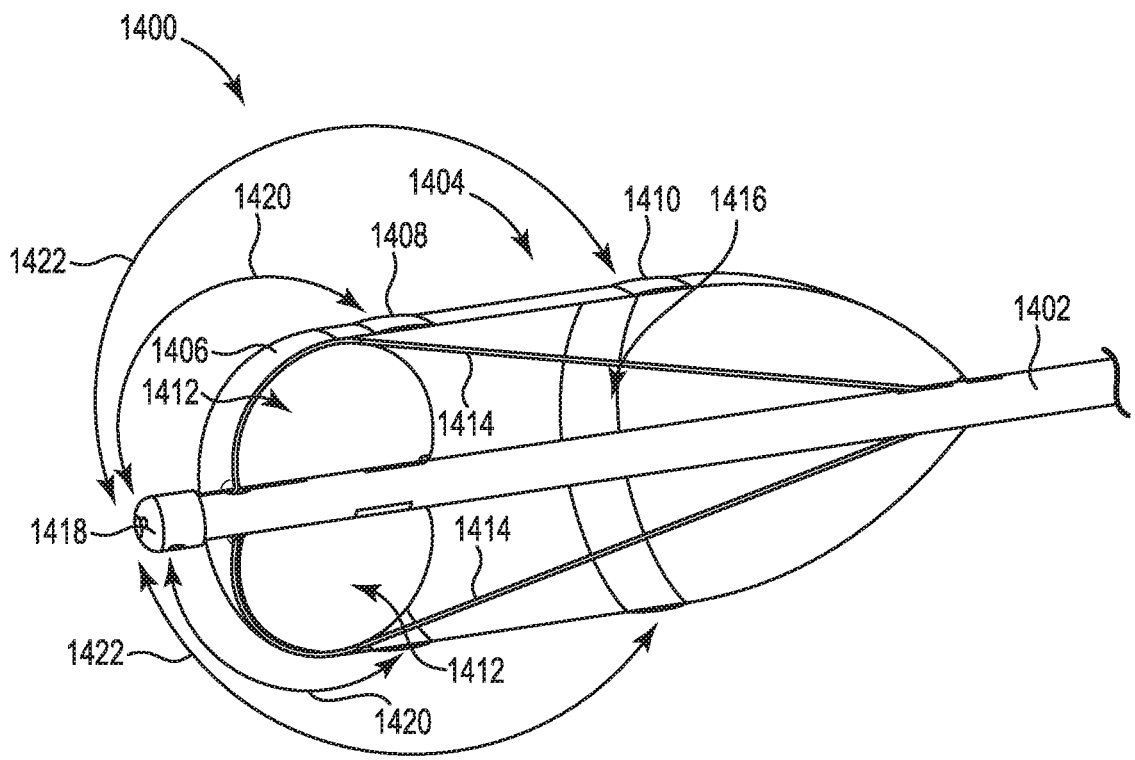

FIGS. 14A and 14B are diagrams illustrating partial cross-sections of another apparatus 1400 for applying ablation therapy to a tissue region, in accordance with embodiments of the disclosure. The apparatus 1400 includes a catheter having an elongate body 1402. In embodiments, the apparatus 1400 may also include a balloon structure 1404 arranged at or near a distal portion of the elongate body 1402.

According to embodiments, the balloon structure 1404 may include a surface having a first portion 1406, a second portion 1408 and a third portion 1410. In embodiments, the permeability of the first portion 1406 may be different than the permeability of the second portion 1408, which may be different than the permeability of the third portion 1410. Alternatively, in embodiments, the permeability of the second portion 1408 may be the same as the permeability of the third portion 1410. The permeability of the first portion 1406 may be referred to as a first permeability, the permeability of the second portion 1408 may be referred to as a second permeability and the permeability of the third portion 1410 may be referred to as a third permeability. In embodiments, the second permeability and the third permeability may be greater than the first permeability. For example, the second portion 1408 and the third portion 1410 of the balloon structure 1404 may be configured to allow a liquid to permeate or elute therethrough (in response to inflation of the balloon structure 1404) and the permeability of the first portion 1406 may be zero such that liquid does not permeate or elute therethrough. In embodiments, the permeability of the second portion 1408 and/or the third portion 1410 may be due to pores in the second portion 1408 and/or the third portion 1410 that may be approximately between 1 millimeter and 10 millimeters in diameter when the balloon structure 1404 is inflated. In embodiments, the permeability of the second and third portions 1408, 1410 may contribute to delivering ablation energy to target tissue, as discussed below.

In embodiments, the second and third portions 1408, 1410 may have a strip shape that circumferentially extends around the balloon structure 1404. Alternatively, the second portion 1408 and/or the third portion 1410 may have other shapes including, for example, circles, ellipses, quadrilaterals, triangles, and/or the like. Additionally or alternatively, the second and third portions 1408, 1410 may be located at different axial positions of the balloon structure 1404 and/or be located at different radial positions of the balloon structure 1404.

In embodiments, the balloon structure 1404 may be positioned near a target tissue region for ablation. The tissue region may be a vessel such as a pulmonary vein, renal vein, portion of the liver, portion of the esophagus and/or other appendage. After positioning the balloon structure 1404 near a target tissue region, the balloon structure 1404 may be deployed. For example, the balloon structure 1404 may be configured to inflate in response to a liquid or inflation medium being provided thereto. In embodiments, the balloon structure 1404 may include a chamber 1412 which is configured to inflate in response to a liquid or inflation medium being provided thereto. Once inflated, the chamber 1410 may push electrodes 1414 towards the exterior of the apparatus 1400 in order to facilitate delivering ablative energy to a tissue region, as described in more detail below. Additionally or alternatively, the chamber 1410, once inflated, may facilitate anchoring the balloon structure 1404 to a tissue region. For example, the chamber 1410 may position and/or anchor the second portion 1408 against a target tissue region. In embodiments, the chamber 1412 may be located near a proximal portion of the balloon structure 1404, as depicted in FIG. 14A, or near a distal portion of the balloon structure 1404, as depicted in FIG. 14B.

Additionally or alternatively, the balloon structure 1404 may include a chamber 1416 that may also be inflated in response to a liquid or other inflation medium. After being inflated, the second portion 1408 and/or third portion 1410 of the balloon structure 1404 may contact a target tissue region. In embodiments, the second portion 1408 and/or the third portion 1410 may form part of the chamber 1416 (e.g., a wall of the chamber 1416) and/or the second portion 1408 and/or the third portion 1410 and the chamber 1416 may be in fluid communication with one another. As such, once the chamber 1416 is inflated, the liquid and/or other inflation medium may permeate through the second portion 1408 and/or the third portion 1410. In embodiments, a consistent supply of liquid and/or another inflation medium may be delivered to the chamber 1416 to substantially offset any liquid and/or other inflation medium that permeates through the second portion 1408 and/or the third portion 1410.

According to embodiments, the apparatus 1400 may include one or more electrodes 1414 arranged within the balloon structure 1404. In embodiments, the electrodes 1414 may be used to delivery ablative energy to a tissue region. For example, an external source/controller may apply a voltage to the electrodes 1414 via one or more conductive wires internal to the elongate body 1402. In response to the voltage being applied to the electrodes 1414, an electric field may be generated between the electrodes 1414 and a second electrode having a ground electrical potential and/or lower electric potential than the electrodes 1414. The electric field generated between the electrodes 1414 and a second electrode elicits a current that passes through a tissue region. In embodiments, the current may be delivered via a liquid and/or other inflation medium of the chamber 1416, through the second portion 1408 (since the liquid and/or other inflation medium can permeate the second portion 1408), and to the tissue region (e.g., the vessel wall). Additionally or alternatively, the current may be delivered via a liquid and/or other inflation medium of the chamber 1416, through the third portion 1410 (since the liquid and/or other inflation medium can permeate the third portion 1410), and to the tissue region (e.g., the vessel wall). The delivered current may modulate the activity along neural fibers within the wall of the tissue by at least partially causing apoptotic cell death to the tissue receiving the ablation energy. Additionally or alternatively, the electrodes 1414 may be grounded and/or held at a lower electric potential than the second electrode to facilitate current flowing from the second electrode to the electrodes 1414. As such, in embodiments, current may flow from the second electrode to the electrodes 1414 and/or vice versa. In response, an electric field generated between the second electrode and the electrodes 1414 may elicit a current that passes from the second electrode through the second portion 1408 to the electrodes 1414 via the tissue and the liquid and/or other inflation medium of the chamber 1416. Additionally or alternatively, one or more metal portions of the elongate body 1402 may be used to generate the electric field used to ablate tissue.

According to embodiments, the majority of the current will not pass through the first portion 1406 of the balloon structure 1404 since the liquid and/or other inflation medium of the chamber 1416 cannot permeate the first portion 1406. Therefore, based on the position of the second portion 1408 and/or the third portion 1410 relative to the tissue, the current produced by the electrodes 1414 may be applied to tissue in a controlled and localized manner.

In embodiments, a tip electrode 1418 may be used as the second electrode to form a ground and/or a closed-loop with the electrodes 1414. In embodiments where the tip electrode 1418 is used as the second electrode, a current may be generated between the electrodes 1414 and the tip electrode 1418 via the second portion 1408, as indicated by the arrows 1420. Additionally, in embodiments where the tip electrode 1418 is used as the second electrode, a current may be generated between the electrodes 1414 and the tip electrode 1418 via the third portion 1408, as indicated by the arrows 1422. In embodiments, the tip electrode 1418 may also be coupled to the external source/controller.

According to embodiments, the electrodes 1414 may be configured to determine electrical activity of the tissue region. For example, the electrodes 1414 may be used prior to ablation to estimate an extent of tissue damage. Additionally or alternatively, the electrodes 1414 may be used after the ablation to determine the extent of the ablation. According to embodiments, the electrodes 1414 may be electrically coupled to a mapping signal processor such that electrical events in myocardial tissue can be sensed for the generation of electrograms, monophasic action potentials (MAPs), isochronal electrical activity maps, and the like. As such, the electrodes 1414 may allow the physician to measure the electrical activity of the tissue region (e.g., the lack of near-field electrical activity may indicate ablated tissue, whereas the presence of near-field electrical activity may indicate live tissue) and determine a target location for the ablation therapy.

In embodiments, the apparatus 1400 may be steerable and include one or more steering wires (not shown) located internal to the elongate body 1402. The steering wires may be configured to direct the balloon structure 1404, the elongate body 1402, or both. The steering wires may be arranged within a central lumen (not shown) of the elongate body 1402. The steering wires may direct the balloon structure 1404 and/or the elongate body 1402 in multiple directions based on a force applied thereto. The steering wires may be coupled to a catheter handle (e.g., as shown in FIG. 1). Additionally or alternatively, lumens disposed on one or more sides of the central lumen may be used to transport liquid to each of the chambers 1412, 1416.

The illustrative apparatus 1400 shown in FIGS. 14A and 14B is not intended to suggest any limitation as to the scope of use or functionality of embodiments of the present disclosure. Neither should the illustrative apparatus 1400 be interpreted as having any dependency nor requirement related to any single component or combination of components illustrated therein. Additionally, various components depicted in FIG. 14 may be, in embodiments, integrated with various ones of the other components depicted therein (and/or components not illustrated), all of which are considered to be within the ambit of the present disclosure.

Figure 15:
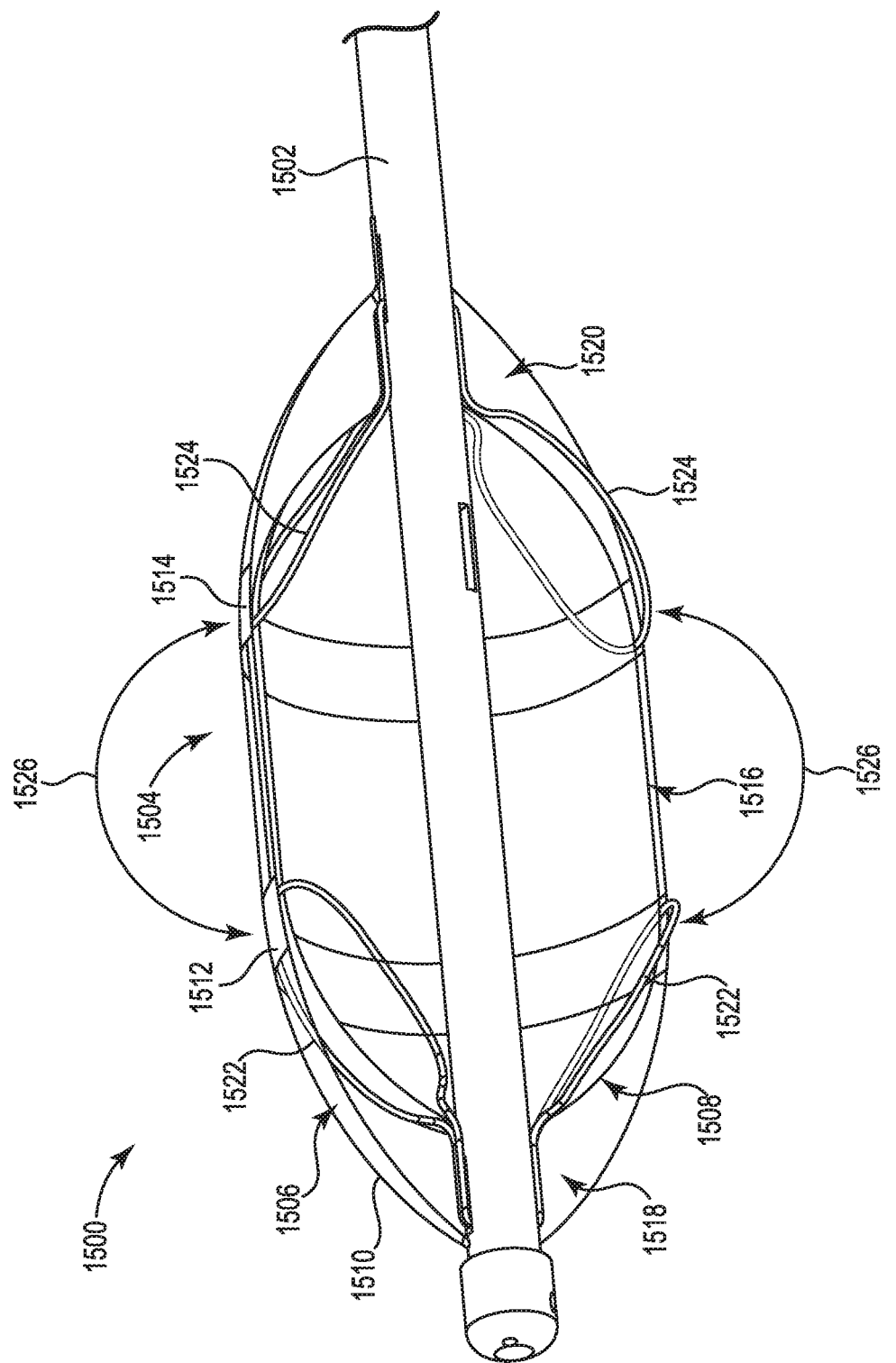
FIG. 15 a diagram illustrating a partial cross-section of another apparatus for applying ablation therapy to a tissue region, in accordance with embodiments of the disclosure.

FIG. 15 is a diagram illustrating a partial cross-section of another apparatus 1500 for applying ablation therapy to a tissue region, in accordance with embodiments of the disclosure. The apparatus 1500 includes a catheter having an elongate body 1502. In embodiments, the apparatus 1500 may also include a balloon structure 1504 arranged at or near a distal portion of the elongate body 1502.

According to embodiments, the balloon structure 1504 may include two balloon structures an outer balloon structure 1506 and an inner balloon structure 1508. In embodiments, the outer balloon structure 1506 may have a first portion 1510, a second portion 1512 and a third portion 1514. In embodiments, the permeability of the first portion 1510 may be different than the permeability of the second portion 1512, which may be different than the permeability of the third portion 1514. Alternatively, in embodiments, the permeability of the second portion 1512 may be the same as the permeability of the third portion 1514. The permeability of the first portion 1510 may be referred to as a first permeability, the permeability of the second portion 1512 may be referred to as a second permeability and the permeability of the third portion 1514 may be referred to as a third permeability. In embodiments, the second permeability and the third permeability may be greater than the first permeability. For example, the second portion 1512 and the third portion 1514 of the outer balloon structure 1506 may be configured to allow a liquid to permeate or elute therethrough (in response to inflation of the balloon structure 1504) and the permeability of the first portion 1510 may be zero such that liquid does not permeate or elute therethrough. In embodiments, the permeability of the second portion 1512 and/or the third portion 1514 may be due to pores in the second portion 1512 and/or the third portion 1514 that may be approximately between 1 millimeter and 10 millimeters in diameter when the balloon structure 1504 is inflated. In embodiments, the permeability of the second and third portions 1512, 1514 may contribute to delivering ablation energy to target tissue, as discussed below.

In embodiments, the second and third portions 1512, 1514 may have a strip shape that circumferentially extends around the outer balloon structure 1506. Alternatively, the second portion 1512 and/or the third portion 1514 may have other shapes including, for example, circles, ellipses, quadrilaterals, triangles, and/or the like. Additionally or alternatively, the second and third portions 1512, 1514 may be located at different axial positions of the outer balloon structure 1506 and/or be located at different radial positions of the outer balloon structure 1506

In embodiments, the balloon structure 1504 may be positioned near a target tissue region for ablation. The tissue region may be a vessel such as a pulmonary vein, renal vein, portion of the liver, portion of the esophagus and/or other appendage. After positioning the balloon structure 1504 near a target tissue region, the balloon structure 1504 may be deployed. For example, the inner balloon structure 1508 may be configured to inflate in response to a liquid or inflation medium being provided thereto. Once inflated, the inner balloon structure 1508 may anchor the balloon structure 1504 to a tissue region. In addition, once the balloon structure 1504 is inflated, the second portion 1512 and/or third portion 1514 may contact a target tissue region.

In embodiments, the inner balloon structure 1508 may be sealed to the outer balloon structure 1506 at a central axial portion 1516 of the balloon structure 1504. The seal may extend circumferentially around the outer and inner balloon structures 1506, 1508, so that two different chambers 1518, 1520 located between the outer and inner balloon structures 1506, 1508 is created.

In embodiments, the second portion 1512 may form part of the chamber 1518 (e.g., a wall of the chamber 1518) and/or the second portion 1512 and the chamber 1518 may be in fluid communication with one another. As such, once the chamber 1518 is inflated, the liquid and/or other inflation medium used to inflate the chamber 1518 may permeate through the second portion 1512. In embodiments, a consistent supply of liquid and/or another inflation medium may be delivered to the chamber 1518 to substantially offset any liquid and/or other inflation medium that permeates through the second portion 1512.

Additionally or alternatively, the third portion 1514 may form part of the chamber 1520 (e.g., a wall of the chamber 1520) and/or the third portion 1514 and the chamber 1520 may be in fluid communication with one another. As such, once the chamber 1520 is inflated, the liquid and/or other inflation medium used to inflate the chamber 1520 may permeate through the third portion 1514. In embodiments, a consistent supply of liquid and/or another inflation medium may be delivered to the chamber 1520 to substantially offset any liquid and/or other inflation medium that permeates through the third portion 1514.

According to embodiments, the apparatus 1500 may include one or more electrodes 1522 arranged within the chamber 1518 of the balloon structure 1504. In embodiments, the electrodes 1522 may be used to delivery ablative energy to a tissue region. For example, an external source/controller may apply a voltage to the electrodes 1522 via one or more wires internal to the elongate body 1502. In response to the voltage being applied to the electrodes 1522, an electric field may be generated between the electrodes 1522 and a second electrode having a ground electrical potential and/or lower electric potential than the electrodes 1522. The electric field generated between the electrodes 1522 and a second electrode elicits a current that passes through a tissue region. In embodiments, the current may be delivered via a liquid and/or other inflation medium of the chamber 1518, through the second portion 1512 (since the liquid and/or other inflation medium can permeate the second portion 1512), and to the tissue region (e.g., the vessel wall). The delivered current may modulate the activity along neural fibers within the wall of the tissue by at least partially causing apoptotic cell death to the tissue receiving the ablation energy.

Additionally or alternatively, the electrodes 1522 may be grounded and/or held at a lower electric potential than a second electrode to facilitate current flowing from a second electrode to the electrodes 1522. As such, in embodiments, current may flow from the second electrode to the electrodes 1522 and vice-versa. In response, an electric field generated between the second electrode and the electrodes 1522 may elicit a current that passes from the second electrode through the second portion 1512 to the electrodes 1522 via the tissue and the liquid and/or other inflation medium of the chamber 1518.

Additionally or alternatively, the apparatus 1500 may include one or more electrodes 1524 arranged within the chamber 1520 of the balloon structure 1504. Similar to the electrodes 1522, the electrodes 1524 may be used to delivery ablative energy to a tissue region. For example, an external source/controller may apply a voltage to the electrodes 1524 via one or more wires internal to the elongate body 1502. In response to the voltage being applied to the electrodes 1524, an electric field may be generated between the electrodes 1524 and a second electrode having a ground electrical potential and/or lower electric potential than the electrodes 1524. The electric field generated between the electrodes 1524 and a second electrode elicits a current that passes through a tissue region. In embodiments, the current may be delivered via a liquid and/or other inflation medium of the chamber 1520, through the third portion 1514 (since the liquid and/or other inflation medium can permeate the third portion 1514), and to the tissue region (e.g., the vessel wall). The delivered current may modulate the activity along neural fibers within the wall of the tissue by at least partially causing apoptotic cell death to the tissue receiving the ablation energy.

Additionally or alternatively, the electrodes 1524 may be grounded and/or held at a lower electric potential than a second electrode to facilitate current flowing from a second electrode to the electrodes 1524. As such, in embodiments, current may flow from the electrodes 1524 to the second electrode and/or from the second electrode to the electrodes 1524. In response, an electric field generated between the second electrode and the electrodes 1524 may elicit a current that passes from the second electrode through the third portion 1514 to the electrodes 1524 via the tissue and the liquid and/or other inflation medium of the chamber 1520.

According to embodiments, the majority of the current will not pass through the first portion 1510 of the balloon structure 1504 since the liquid and/or other inflation medium of the chambers 1518, 1520 cannot permeate the first portion 1510. Therefore, based on the position of the second portion 1512 and/or the third portion 1514 relative to the tissue, the current produced by the electrodes 1522, 1524 may be applied to tissue in a controlled and localized manner.

In embodiments, the electrodes 1522, 1524 may act as a pair. That is, for example, the electrode 1522 may act as the second electrode to the electrode 1524 and/or vice versa, so that the electrodes 1522, 1524 form a ground and/or a closed-loop with each other. In embodiments where the electrode 1522 is used as the second electrode to the electrode 1524 or vice versa, a current may be generated between the electrodes 1522, 1524 via the second and third portions 1512, 1514, as indicated by the arrows 1526.

According to embodiments, the electrodes 1522, 1524 may be configured to determine electrical activity of the tissue region. For example, the electrodes 1522, 1524 may be used prior to ablation to estimate an extent of tissue damage. Additionally or alternatively, the electrodes 1522, 1524 may be used after the ablation to determine the extent of the ablation. According to embodiments, the electrodes 1522, 1524 may be electrically coupled to a mapping signal processor such that electrical events in myocardial tissue can be sensed for the generation of electrograms, monophasic action potentials (MAPs), isochronal electrical activity maps, and the like. As such, the electrodes 1522, 1524 may allow the physician to measure the electrical activity of the tissue region (e.g., the lack of near-field electrical activity may indicate ablated tissue, whereas the presence of near-field electrical activity may indicate live tissue) and determine a target location for the ablation therapy.

In embodiments, the apparatus 1500 may be steerable and include one or more steering wires (not shown) located internal to the elongate body 1502. The steering wires may be configured to direct the balloon structure 1504, the elongate body 1502, or both. The steering wires may be arranged within a central lumen (not shown) of the elongate body 1502. The steering wires may direct the balloon structure 1504 and/or the elongate body 1502 in multiple directions based on a force applied thereto. The steering wires may be coupled to a catheter handle (e.g., as shown in FIG. 1). Additionally or alternatively, lumens disposed on one or more sides of the central lumen may be used to transport liquid to the outer balloon chamber 1506, the inner balloon chamber 1508 and/or the chambers 1518, 1520.

The central lumen may include portions that carry liquid to the outer balloon chamber 1506, the inner balloon chamber 1508, and/or the chambers 1518, 1520. The illustrative apparatus 1500 shown in FIG. 15 is not intended to suggest any limitation as to the scope of use or functionality of embodiments of the present disclosure. Neither should the illustrative apparatus 1500 be interpreted as having any dependency nor requirement related to any single component or combination of components illustrated therein. Additionally, various components depicted in FIG. 15 may be, in embodiments, integrated with various ones of the other components depicted therein (and/or components not illustrated), all of which are considered to be within the ambit of the present disclosure.

Figure 16:
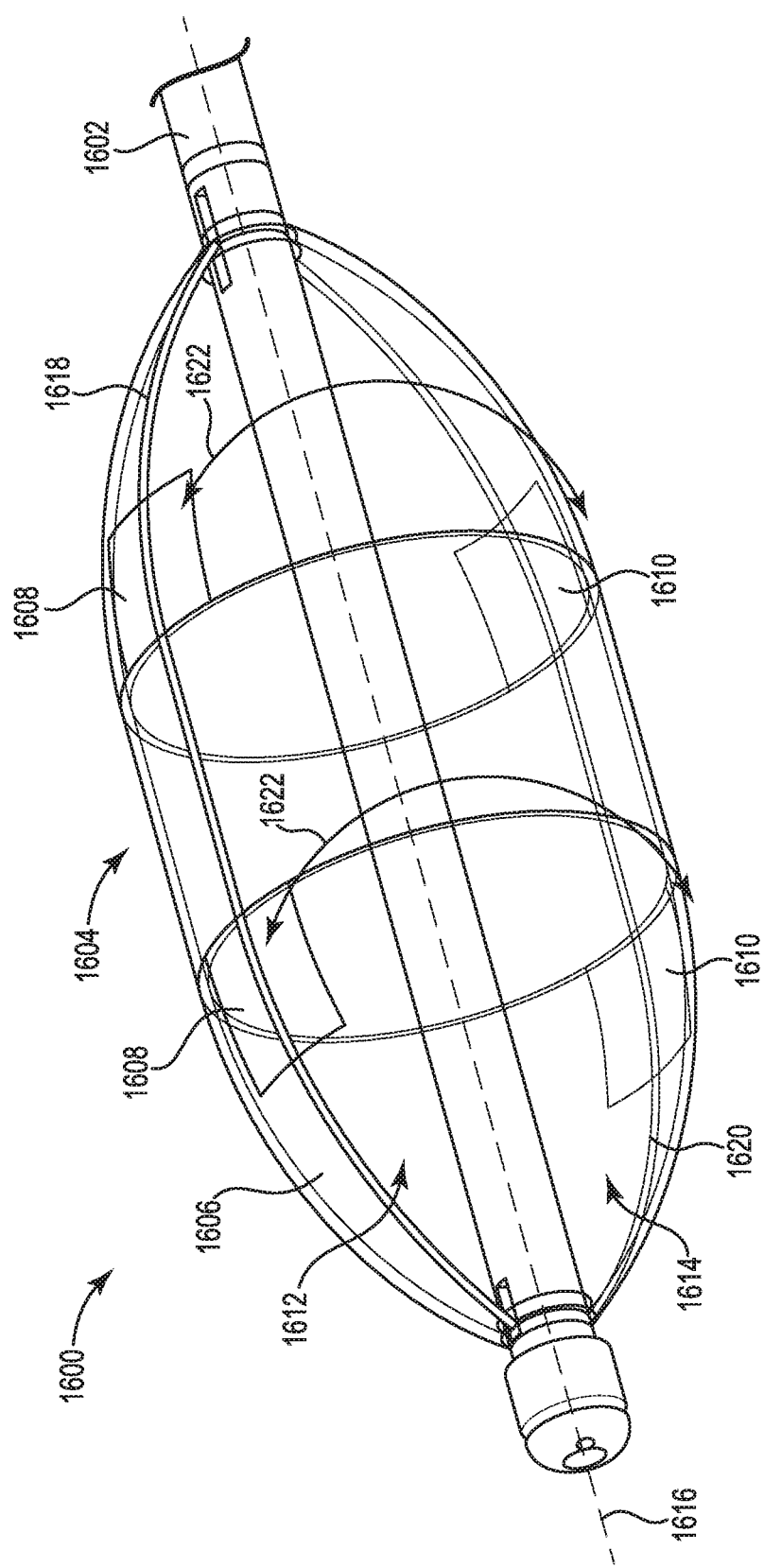
FIG. 16 a diagram illustrating a perspective view of another apparatus for applying ablation therapy to a tissue region, in accordance with embodiments of the disclosure.

FIG. 16 a diagram illustrating a perspective view of another apparatus 1600 for applying ablation therapy to a tissue region, in accordance with embodiments of the disclosure. The apparatus 1600 includes a catheter having an elongate body 1602. In embodiments, the apparatus 1600 may also include a balloon structure 1604 arranged at or near a distal portion of the elongate body 1602.

According to embodiments, the balloon structure 1604 may have a first portion 1606, a second portion 1608 and a third portion 1610. In embodiments, the second portion 1608 may include a plurality of second portions 1608, as shown in FIG. 16. Additionally or alternatively, the third portion 1610 may include a plurality of third portions 1610, as shown in FIG. 16. In embodiments, each second portion 1608 may form a respective pair with a third portion 1610, and form a closed-loop circuit, as described in more detail below.

In embodiments, the permeability of the first portion 1606 may be different than the permeability of the second portion 1608, which may be different than the permeability of the third portion 1610. Alternatively, in embodiments, the permeability of the second portion 1608 may be the same as the permeability of the third portion 1610. The permeability of the first portion 1606 may be referred to as a first permeability, the permeability of the second portion 1608 may be referred to as a second permeability and the permeability of the third portion 1610 may be referred to as a third permeability. In embodiments, the second permeability and the third permeability may be greater than the first permeability. For example, the second portion 1608 and the third portion 1610 of the balloon structure 1604 may be configured to allow a liquid to permeate or elute therethrough (in response to inflation of the balloon structure 1604) and the permeability of the first portion 1606 may be zero such that liquid does not permeate or elute therethrough. In embodiments, the permeability of the second portion 1608 and/or the third portion 1610 may be due to pores in the second portion 1608 and/or the third portion 1610 that may be approximately between 1 millimeter and 10 millimeters in diameter when the balloon structure 1604 is inflated. In embodiments, the permeability of the second and third portions 1608, 1610 may contribute to delivering ablation energy to target tissue, as discussed below.

In embodiments, the second and third portions 1608, 1610 may have a quadrilateral shape and may be located at different radial positions of the balloon structure 1604. Alternatively, the second portion 1608 and/or the third portion 1610 may have other shapes including, for example, circles, ellipses, quadrilaterals, triangles, and/or the like. Additionally or alternatively, the second and third portions 1608, 1610 may be located at different axial positions of the outer balloon structure 1604.

In embodiments, the balloon structure 1604 may be positioned near a target tissue region for ablation. The tissue region may be a vessel such as a pulmonary vein, renal vein, portion of the liver, portion of the esophagus and/or other appendage. After positioning the balloon structure 1604 near a target tissue region, the balloon structure 1604 may be deployed. For example, the balloon structure 1604 may include an inner balloon structure that is configured to inflate in response to a liquid or inflation medium being provided thereto. Once inflated, the inner balloon structure may anchor the balloon structure 1604 to a tissue region. In addition, once the balloon structure 1604 is inflated, the second portion 1608 and/or third portion 1610 may contact a target tissue region.

In embodiments, the inner balloon structure may be sealed to an outer balloon structure of the balloon structure 1604, so that the balloon structure 1604 is separated into an upper chamber 1612 and a lower chamber 1614, which are in fluid isolation of one another. The upper and lower chambers 1612, 1614 are separated by the dotted line 1616 depicted in FIG. 16.

In embodiments, the second portion 1608 may form part of the upper chamber 1612 (e.g., a wall of the upper chamber 1612) and/or the second portion 1608 and the upper chamber 1612 may be in fluid communication with one another. As such, once the upper chamber 1612 is inflated, the liquid and/or other inflation medium used to inflate the upper chamber 1612 may permeate through the second portion 1608. In embodiments, a consistent supply of liquid and/or another inflation medium may be delivered to the upper chamber 1612 to substantially offset any liquid and/or other inflation medium that permeates through the second portion 1608.

Additionally or alternatively, the third portion 1610 may form part of the lower chamber 1614 (e.g., a wall of the lower chamber 164) and/or the third portion 1610 and the lower chamber 1614 may be in fluid communication with one another. As such, once the lower chamber 1614 is inflated, the liquid and/or other inflation medium used to inflate the lower chamber 1614 may permeate through the third portion 1610. In embodiments, a consistent supply of liquid and/or another inflation medium may be delivered to the lower chamber 1614 to substantially offset any liquid and/or other inflation medium that permeates through the third portion 1610.

According to embodiments, the apparatus 1600 may include one or more electrodes 1618 arranged within the upper chamber 1612 of the balloon structure 1604. In embodiments, the electrodes 1618 may be used to delivery ablative energy to a tissue region. For example, an external source/controller may apply a voltage to the electrodes 1618 via one or more wires internal to the elongate body 1602. In response to the voltage being applied to the electrodes 1618, an electric field may be generated between the electrodes 1618 and a second electrode having a ground electrical potential and/or lower electric potential than the electrodes 1618. The electric field generated between the electrodes 1618 and a second electrode elicits a current that passes through a tissue region. In embodiments, the current may be delivered via a liquid and/or other inflation medium of the lower chamber 1614, through the second portion 1608 (since the liquid and/or other inflation medium can permeate the second portion 1608), and to the tissue region (e.g., the vessel wall). The delivered current may modulate the activity along neural fibers within the wall of the tissue by at least partially causing apoptotic cell death to the tissue receiving the ablation energy.

Additionally or alternatively, the electrodes 1618 may be grounded and/or held at a lower electric potential than a second electrode to facilitate current flowing from the second electrode to the electrodes 1618. As such, in embodiments, current may flow from the second electrode to the electrodes 1618 and/or vice versa. In response, an electric field generated between the second electrode and the electrodes 1618 may elicit a current that passes from the second electrode through the second portion 1608 to the electrodes 1618 via the tissue and the liquid and/or other inflation medium of the upper chamber 1612.

Additionally or alternatively, the apparatus 1600 may include one or more electrodes 1620 arranged within the lower chamber 1614 of the balloon structure 1604. Similar to the electrodes 1618, the electrodes 1620 may be used to delivery ablative energy to a tissue region. For example, an external source/controller may apply a voltage to the electrodes 1620 via one or more wires internal to the elongate body 1602. In response to the voltage being applied to the electrodes 1620, an electric field may be generated between the electrodes 1620 and a second electrode having a ground electrical potential and/or lower electric potential than the electrodes 1620. The electric field generated between the electrodes 1620 and a second electrode elicits a current that passes through a tissue region. In embodiments, the current may be delivered via a liquid and/or other inflation medium of the lower chamber 1614 through the third portion 1610 (since the liquid and/or other inflation medium can permeate the third portion 1610), and to the tissue region (e.g., the vessel wall). The delivered current may modulate the activity along neural fibers within the wall of the tissue by at least partially causing apoptotic cell death to the tissue receiving the ablation energy.

Additionally or alternatively, the electrodes 1620 may be grounded and/or held at a lower electric potential than a second electrode to facilitate current flowing from a second electrode to the electrodes 1620. As such, in embodiments, current may flow from the second electrode to the electrodes 1620 or vice versa. In response, an electric field generated between the second electrode and the electrodes 1620 may elicit a current that passes from the second electrode through the third portion 1610 to the electrodes 1620 via the tissue and the liquid and/or other inflation medium of the lower chamber 1614.

According to embodiments, the majority of the current will not pass through the first portion 1606 of the balloon structure 1604 since the liquid and/or other inflation medium of the chambers 1612, 1614 cannot permeate the first portion 1606. Therefore, based on the position of the second portion 1608 and/or the third portion 1610 relative to the tissue, the current produced by the electrodes 1618, 1620 may be applied to tissue in a controlled and localized manner.

In embodiments, the each of the electrodes 1618, 1620 may act as pairs. That is, for example, the electrode 1618 may act as the second electrode to the electrode 1620 or vice versa, so that the electrodes 1618, 1620 form a ground and/or a closed-loop with each other. In embodiments where the electrode 1618 is used as the second electrode to the electrode 1620 or vice versa, a current may be generated between the electrodes 1618, 1620 via the second and third portions 1608, 1610, as indicated by the arrows 1622.

According to embodiments, the electrodes 1618, 1620 may be configured to determine electrical activity of the tissue region. For example, the electrodes 1618, 1620 may be used prior to ablation to estimate an extent of tissue damage. Additionally or alternatively, the electrodes 1618, 1620 may be used after the ablation to determine the extent of the ablation. According to embodiments, the electrodes 1618, 1620 may be electrically coupled to a mapping signal processor such that electrical events in myocardial tissue can be sensed for the generation of electrograms, monophasic action potentials (MAPs), isochronal electrical activity maps, and the like. As such, the electrodes 1618, 1620 may allow the physician to measure the electrical activity of the tissue region (e.g., the lack of near-field electrical activity may indicate ablated tissue, whereas the presence of near-field electrical activity may indicate live tissue) and determine a target location for the ablation therapy.

In embodiments, the apparatus 1600 may be steerable and include one or more steering wires (not shown) located internal to the elongate body 1602. The steering wires may be configured to direct the balloon structure 1604, the elongate body 1602, or both. The steering wires may be arranged within a central lumen (not shown) of the elongate body 1602. The steering wires may direct the balloon structure 1604 and/or the elongate body 1602 in multiple directions based on a force applied thereto. The steering wires may be coupled to a catheter handle (e.g., as shown in FIG. 1). Additionally or alternatively, lumens disposed on one or more sides of the central lumen may be used to transport liquid to the balloon structure 1604 and/or the chambers 1612, 1614.

The illustrative apparatus 1600 shown in FIG. 16 is not intended to suggest any limitation as to the scope of use or functionality of embodiments of the present disclosure. Neither should the illustrative apparatus 1600 be interpreted as having any dependency nor requirement related to any single component or combination of components illustrated therein. Additionally, various components depicted in FIG. 16 may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An apparatus for applying ablation therapy to a tissue region, the apparatus comprising:
    a catheter having an elongate body extending between a proximal end and a distal end;
    a balloon structure arranged near the distal end, the balloon structure comprising:
        a first portion having a first permeability;
        a second portion having a second permeability; and
        a third portion having a third permeability,
        the first portion being disposed between the second and third portions,
        the first permeability differing from the second permeability,
        the first permeability differing from the third permeability,
        the second and third portions being arranged along an external surface of the balloon structure and having a quadrilateral shape,
        the second and third portions having similar axial positions along the balloon structure and having different radial positions along the balloon structure; and
    a first electrode arranged on or within the balloon structure and configured to transmit or receive a current, wherein the current is transmitted or received through the second portion of the balloon structure via a liquid permeating the second portion, wherein the liquid cannot permeate the first portion.

2. The apparatus of claim 1, the liquid comprising at least one of saline, a pharmacological agent, a contrast agent, and an anti-stenotic agent.

3. The apparatus of claim 1, the second permeability being due to the second portion having pores between approximately 1 millimeter and 10 millimeters when the balloon structure is in an expanded configuration.

4. The apparatus of claim 1, the second portion having a strip shape extending circumferentially around the balloon structure.

5. The apparatus of claim 1, the second permeability being substantially the same as the third permeability.

6. The apparatus of claim 1, the first, second and third portions being arranged along an external surface of the balloon structure.

7. The apparatus of claim 1, the second portion having a strip shape extending circumferentially around the balloon structure and the third portion having a strip shape extending circumferentially around the balloon structure, wherein the second and third portions have different axial positions along the balloon structure.

8. The apparatus of claim 1, the second portion comprising a plurality of second portions and the third portion comprising a plurality of third portions, wherein each third portion of the plurality of third portions forms a pair with a respective second portion of the plurality of second portions.

9. The apparatus of claim 1, further comprising a second electrode arranged on the distal end of the catheter, the second electrode configured to: receive the transmitted current of the first electrode or transmit the current received by the first electrode.

10. The apparatus of claim 1, wherein a current is transmitted or received through the third portion of the balloon structure via a liquid permeating the third portion.

11. The apparatus of claim 10, the balloon structure having a first chamber in fluid communication with the second portion and the balloon structure having a second chamber in fluid communication with the third portion, wherein the first and second chambers are in fluid isolation of one another.

12. The apparatus of claim 11, further comprising a second electrode arranged on or within the second chamber, wherein a current is at least one of: transmitted by the first electrode and received by the second electrode, and transmitted by the second electrode and received by the first electrode.

13. An apparatus for applying ablation therapy to a tissue region, the apparatus comprising:
    a catheter having an elongate body extending between a proximal end and a distal end;
    a balloon structure arranged near the distal end, the balloon structure comprising:
        a first portion having a first permeability;
        a second portion having a second permeability;
        a third portion having a third permeability;
        a first chamber in fluid communication with the second portion; and
        a second chamber in fluid communication with the third portion,
        the second and third portions having: (i) similar axial positions along the balloon structure, (ii) different radial positions along the balloon structure, and (iii) quadrilateral shapes;
    a first electrode in fluid communication with the first chamber; and
    a second electrode in fluid communication with the second chamber, wherein the first and second electrodes are configured to conduct a current therebetween via a liquid that permeates the second and third portions, wherein the liquid cannot permeate the first portion.

14. The apparatus of claim 13, the liquid comprising at least one of saline, a pharmacological agent, a contrast agent, and an anti-stenotic agent.

15. The apparatus of claim 13, the second permeability being due to the second portion having pores between approximately 1 millimeter and 10 millimeters when the balloon structure is in an expanded configuration and the third permeability being due to the third portion having pores between approximately 1 millimeter and 10 millimeters when the balloon structure is in an expanded configuration.

16. The apparatus of claim 13, the second portion having a strip shape extending circumferentially around the balloon structure and the third portion having a strip shape extending circumferentially around the balloon structure, wherein the second and third portions have different axial positions along the balloon structure.

\* \* \* \* \*